US012698274B2

(12) United States Patent
(10) Patent No.: US 12,698,274 B2
(45) Date of Patent: Aug. 4, 2026

Han et al.

(54) BENZIMIDAZOLE-SUBSTITUTED FLUORANTHENE COMPOUND, AND ORGANIC LIGHT EMITTING DEVICE INCLUDING THE SAME

(71) Applicant: LG CHEM, LTD., Seoul (KR)

(72) Inventors: Miyeon Han, Daejeon (KR); Sung Kil Hong, Daejeon (KR); Dong Uk Heo, Daejeon (KR); Jung Min Yoon, Daejeon (KR); Heekyung Yun, Daejeon (KR)

(73) Assignee: LG CHEM, LTD., Seoul (KR)

( * ) Notice: Subject to any disclaimer, the term of this patent is extended or adjusted under 35 U.S.C. 154(b) by 946 days.

(21) Appl. No.: 17/922,827

(22) PCT Filed: May 14, 2021

(86) PCT No.: PCT/KR2021/006051

§ 371 (c)(1),
(2) Date: Nov. 2, 2022

(87) PCT Pub. No.: WO2022/010087

PCT Pub. Date: Jan. 13, 2022

(65) Prior Publication Data

US 2023/0257356 A1 Aug. 17, 2023

(30) Foreign Application Priority Data

Jul. 10, 2020 (KR) ........................ 10-2020-0085317

(51) Int. Cl.
*H01L 51/50* (2006.01)
*C07D 235/08* (2006.01)
(Continued)

(52) U.S. Cl.
CPC ......... *C07D 405/04* (2013.01); *C07D 235/08* (2013.01); *C07D 401/14* (2013.01);
(Continued)

(58) Field of Classification Search
None
See application file for complete search history.

(56) References Cited

U.S. PATENT DOCUMENTS

| | | | | |
|---|---|---|---|---|
| 9,126,943 | B2 | 9/2015 | Kawamura et al. | |
| 10,026,901 | B2 | 7/2018 | Huang et al. | |
| 2012/0132899 | A1 * | 5/2012 | Kawamura .......... | C07D 403/04 257/E51.026 |

FOREIGN PATENT DOCUMENTS

| | | |
|---|---|---|
| CN | 110128349 | 8/2019 |
| JP | 2018-172319 | 11/2018 |

(Continued)

*Primary Examiner* — Gregory D Clark
(74) *Attorney, Agent, or Firm* — Bryan Cave Leighton Paisner LLP

(57) ABSTRACT

Provided is a benzimidazole-substituted fluoranthene compound of Chemical Formula 1:

[Chemical Formula 1]

(Continued)

where the substituents are as described in the specification, and an organic light emitting device including the same.

7 Claims, 1 Drawing Sheet

(51) Int. Cl.

| | |
|---|---|
| ***C07D 401/14*** | (2006.01) |
| ***C07D 403/04*** | (2006.01) |
| ***C07D 403/10*** | (2006.01) |
| ***C07D 405/04*** | (2006.01) |
| ***C07D 409/04*** | (2006.01) |
| ***H10K 85/60*** | (2023.01) |
| *H10K 50/17* | (2023.01) |

(52) U.S. Cl.
CPC ......... *C07D 403/04* (2013.01); *C07D 403/10* (2013.01); *C07D 409/04* (2013.01); *H10K 85/615* (2023.02); *H10K 85/622* (2023.02); *H10K 85/654* (2023.02); *H10K 85/6572* (2023.02); *H10K 85/6574* (2023.02); *H10K 85/6576* (2023.02); *H10K 50/171* (2023.02)

(56) References Cited

FOREIGN PATENT DOCUMENTS

| | | |
|---|---|---|
| KR | 10-2011-0137897 | 12/2011 |
| KR | 10-2012-0115083 | 10/2012 |
| KR | 10-2015-0011348 | 1/2015 |

* cited by examiner

【FIG. 1】
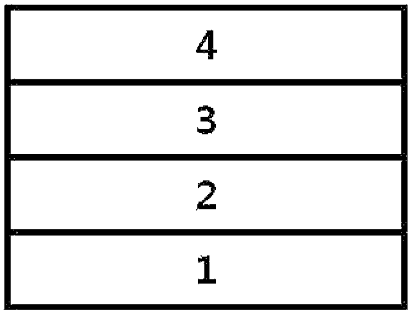
【FIG. 2】
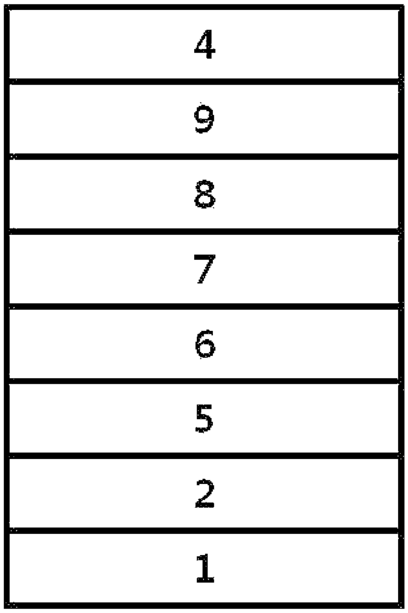

BENZIMIDAZOLE-SUBSTITUTED FLUORANTHENE COMPOUND, AND ORGANIC LIGHT EMITTING DEVICE INCLUDING THE SAME

CROSS-REFERENCE TO RELATED APPLICATIONS

This application is a National Stage Application of International Application No. PCT/KR2021/006051 filed on May 14, 2021, which claims priority to and the benefits of Korean Patent Application No. 10-2020-0085317, filed with the Korean Intellectual Property Office on Jul. 10, 2020, the entire contents of which are incorporated herein by reference.

TECHNICAL FIELD

The present specification relates to a compound, and an organic light emitting device including the same.

BACKGROUND

An organic light emitting device has a structure of disposing an organic thin film between two electrodes. When a voltage is applied to an organic light emitting device having such a structure, electrons and holes injected from the two electrodes bind and pair in the organic thin film, and light emits as these annihilate. The organic thin film can be formed in a single layer or a multilayer as necessary.

A material of the organic thin film can have a light emitting function as necessary. For example, as a material of the organic thin film, compounds capable of forming a light emitting layer themselves alone can be used, or compounds capable of performing a role of a host or a dopant of a host-dopant-based light emitting layer can also be used. In addition thereto, compounds capable of performing roles of hole injection, hole transfer, electron blocking, hole blocking, electron transfer, electron injection or the like can also be used as a material of the organic thin film.

Development of an organic thin film material has been continuously required for enhancing performance, lifetime or efficiency of an organic light emitting device.

BRIEF DESCRIPTION

Technical Problem

The present specification is directed to providing a compound, and an organic light emitting device including the same.

Technical Solution

One embodiment of the present specification provides a compound of the following Chemical Formula 1:

[Chemical Formula 1]

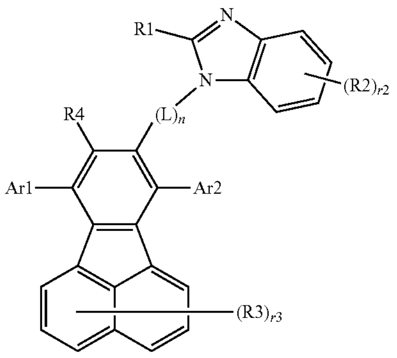

wherein in Chemical Formula 1:

L is a direct bond, a substituted or unsubstituted arylene group, or a substituted or unsubstituted heteroarylene group;

n is 1 or 2, and when n is 2, the Ls are the same as or different from each other;

R1 to R4 are the same as or different from each other, and are each independently hydrogen, deuterium, a substituted or unsubstituted alkyl group, a substituted or unsubstituted aryl group, or a substituted or unsubstituted heteroaryl group;

r2 is an integer of 0 to 4, and when r2 is 2 or greater, the R2s are the same as or different from each other;

r3 is an integer of 0 to 6, and when r3 is 2 or greater, the R3s are the same as or different from each other; and Ar1 and Ar2 are the same as or different from each other, and are each independently deuterium, a substituted or unsubstituted alkyl group, a substituted or unsubstituted aryl group, or a substituted or unsubstituted heteroaryl group.

In addition, one embodiment of the present application provides an organic light emitting device including a first electrode; a second electrode opposite to the first electrode; and one or more organic material layers between the first electrode and the second electrode, wherein one or more layers of the organic material layers include the compound described above.

Advantageous Effects

A compound according to one embodiment of the present application is used in an organic light emitting device, and is thereby capable of increasing luminance, increasing a lifetime, lowering a driving voltage and enhancing light efficiency in the organic light emitting device, and enhancing lifetime properties of the device by thermal stability of the compound.

A fluoranthene structure has strong luminescence intensity in a deep blue region, and has a high photoluminescence quantum yield (PLQY) in both a solution state and a solid state. Through adjusting a conjugation length using various substituents in such a fluoranthene structure, a band gap of the material can be readily adjusted, and through this, energy level properties suitable for a target device structure can be readily adjusted. Accordingly, the compound according to the disclosure of the present application controls the molecular weight by bonding additional substituents to the No. 7 and No. 10 carbons of the fluoranthene, and, compared to a structure having the No. 7 and No. 10 carbons unsubstituted, has a higher glass transition temperature and has properties of excellent thermal stability of the material. In addition, when the bonding position of the benzimidazole is N, electrons are readily transferred in the molecular structure and the device, and low voltage and high efficiency properties can be expected. Particularly, the compound can have excellent properties as an electron control layer, an electron transfer layer or an electron injection layer material.

DESCRIPTION OF THE DRAWINGS

FIG. 1 illustrates an example of an organic light emitting device in which a substrate (1), a first electrode (2), an organic material layer (3) and a second electrode (4) are consecutively laminated.

FIG. 2 illustrates an example of an organic light emitting device in which a substrate (1), a first electrode (2), a hole injection layer (5), a first hole transfer layer (6), a second hole transfer layer (7), a light emitting layer (8), an electron injection and transfer layer (9) and a second electrode (4) are consecutively laminated.

REFERENCE NUMERALS

1: Substrate
2: First Electrode
3: Organic Material Layer
4: Second Electrode
5: Hole Injection Layer
6: First Hole Transfer Layer
7: Second Hole Transfer Layer
8: Light Emitting Layer
9: Electron Injection and Transfer Layer

DETAILED DESCRIPTION

Hereinafter, the present specification will be described in more detail.

One embodiment of the present specification provides a compound of Chemical Formula 1.

In the present specification, a description of a certain member being placed "on" another member includes not only a case of the one member being in contact with the another member but a case of still another member being present between the two members.

In the present specification, a description of a certain part "including" certain constituents means capable of further including other constituents, and does not exclude other constituents unless particularly stated on the contrary.

Throughout the specification of the present application, a term "a combination thereof" included in a Markush-type expression means a mixture or a combination of one or more selected from the group consisting of constituents described in the Markush-type expression, and means including one or more selected from the group consisting of the constituents.

Examples of substituents in the present specification are described below, however, the substituents are not limited thereto.

In the present specification, the term "substitution" means a hydrogen atom bonding to a carbon atom of a compound being changed to another substituent. The position of substitution is not limited as long as it is a position at which the hydrogen atom is substituted, that is, a position at which a substituent can substitute, and when two or more substituents substitute, the two or more substituents can be the same as or different from each other.

In the present specification, the term "substituted or unsubstituted" means being substituted with one or more substituents selected from the group consisting of deuterium, halogen, a cyano group, an alkyl group, a cycloalkyl group, an alkoxy group, an aryloxy group, a silyl group, a boron group, an amine group, a phosphine oxide group, an aryl group, and a heteroaryl group, or being unsubstituted, or being substituted with a substituent linking two or more substituents among the substituents illustrated above, or being unsubstituted.

In the present specification, the term "substituted or unsubstituted" means being substituted with one or more substituents selected from the group consisting of deuterium, a halogen group, a cyano group, an alkyl group, a cycloalkyl group, an alkoxy group, a silyl group, an aryl group, and a heteroaryl group, or being unsubstituted, or being substituted with a substituent linking two or more substituents among the substituents illustrated above, or being unsubstituted.

In the present specification, linking two or more substituents refers to linking hydrogen of any one substituent to another substituent. For example, linking two or more substituents can include a phenyl group and a naphthyl group being linked to become a substituent of

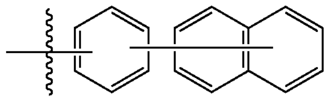
or
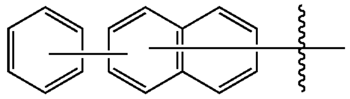

In addition, linking three substituents includes not only continuously linking (substituent 1)-(substituent 2)-(substituent 3), but also linking (substituent 2) and (substituent 3) to (substituent 1). For example, a phenyl group, a naphthyl group and an isopropyl group can be linked to become a substituent of

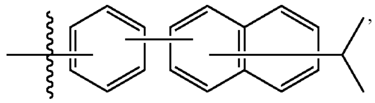
,
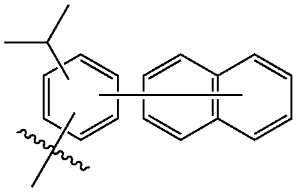
or
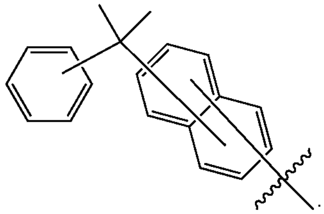
.

The same definition described above also applies when linking four or more substituents.

In the present specification, the halogen group can be fluorine, chlorine, bromine or iodine.

In the present specification, the alkyl group can be linear, branched or cyclic, and although not particularly limited thereto, the number of carbon atoms is preferably from 1 to 50. Specific examples thereof can include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 60 carbon atoms, and specific examples thereof can include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group can be linear, branched or cyclic. The number of carbon atoms of the alkoxy group is not particularly limited, but is preferably from 1 to 30. Specific examples thereof can include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the amine group can be selected from the group consisting of $-NH_2$, a monoalkylamine group, a dialkylamine group, an N-alkylarylamine group, a monoarylamine group, a diarylamine group; an N-arylheteroarylamine group, an N-alkylheteroarylamine group, a monoheteroarylamine group and a diheteroarylamine group, and although not particularly limited thereto, the number of carbon atoms is preferably from 1 to 30. Specific examples of the amine group can include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-phenyltolylamine group, a triphenylamine group, an N-phenylbiphenylamine group, an N-phenylnaphthylamine group; an N-biphenylnaphthylamine group, an N-naphthylfluorenylamine group, an N-phenylphenanthrenylamine group, an N-biphenylphenanthrenylamine group, an N-phenylfluorenylamine group, an N-phenylterphenylamine group, an N-phenanthrenylfluorenylamine group, an N-biphenylfluorenylamine group, and the like, but are not limited thereto.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group.

In the present specification, the alkyl group in the alkylamine group, the N-alkylarylamine group, the alkylthioxy group, the alkylsulfoxy group and the N-alkylheteroarylamine group is the same as the examples of the alkyl group described above. Specific examples of the alkylthioxy group can include a methylthioxy group, an ethylthioxy group, a tert-butylthioxy group, a hexylthioxy group, an octylthioxy group and the like, and specific examples of the alkylsulfoxy group can include mesyl, an ethylsulfoxy group, a propylsulfoxy group, a butylsulfoxy group and the like, however, the alkylthioxy group and the alkylsulfoxy group are not limited thereto.

In the present specification, specific examples of the silyl group can include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group can be $-BR_{100}R_{101}$. $R_{100}$ and $R_{101}$ are the same as or different from each other, and can be each independently selected from the group consisting of hydrogen, deuterium, halogen, a cyano group, a substituted or unsubstituted monocyclic or polycyclic cycloalkyl group having 3 to 30 carbon atoms, a substituted or unsubstituted linear or branched alkyl group having 1 to 30 carbon atoms, a substituted or unsubstituted monocyclic or polycyclic aryl group having 6 to 30 carbon atoms, and a substituted or unsubstituted monocyclic or polycyclic heteroaryl group having 2 to 30 carbon atoms.

In the present specification, specific examples of the phosphine oxide group can include a diphenylphosphine oxide group, a dinaphthylphosphine oxide group and the like, but are not limited thereto.

In the present specification, the aryl group is not particularly limited, but preferably has 6 to 30 carbon atoms, and the aryl group can be monocyclic or polycyclic.

When the aryl group is a monocyclic aryl group in the present specification, the number of carbon atoms is not particularly limited, but is preferably from 6 to 25. Specific examples of the monocyclic aryl group can include a phenyl group, a biphenyl group, a terphenyl group, a quaterphenyl group and the like, but are not limited thereto.

When the aryl group is a polycyclic aryl group, the number of carbon atoms is not particularly limited, but is preferably from 10 to 30. Specific examples of the polycyclic aryl group can include a naphthyl group, an anthracenyl group, a phenanthryl group, a pyrenyl group, a perylenyl group, a chrysenyl group, a fluorenyl group and the like, but are not limited thereto.

In the present specification, the fluorenyl group can be substituted, and adjacent substituents can bond to each other to form a ring.

When the fluorenyl group is substituted,

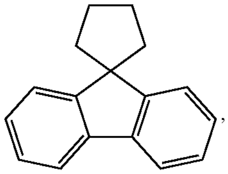,

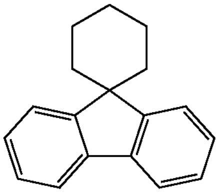,

-continued

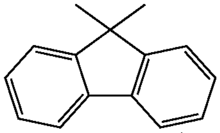,
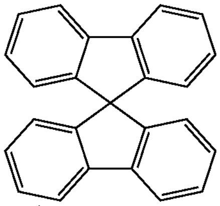,
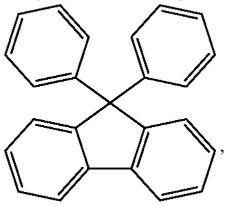, and the like can be included. However, the structure is not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group can be a monocyclic aryl group or a polycyclic aryl group. The arylamine group including two or more aryl groups can include monocyclic aryl groups, polycyclic aryl groups, or both monocyclic aryl groups and polycyclic aryl groups. For example, the aryl group in the arylamine group can be selected from among the examples of the aryl group described above.

In the present specification, the heteroaryl group is a group including one or more atoms that are not carbon, that is, heteroatoms, and specifically, the heteroatom can include one or more atoms selected from the group consisting of O, N, Se, S and the like. The number of carbon atoms of the heteroaryl group is not particularly limited, but is preferably from 2 to 30, and the heteroaryl group can be monocyclic or polycyclic. Examples of the heteroaryl group can include a thiophene group, a furan group, a pyrrole group, an imidazole group, a triazole group, an oxazole group, an oxadiazole group, a pyridine group, a pyrimidine group, a triazine group, a triazole group, a quinolinyl group, a quinazoline group, a carbazole group, a benzoxazole group, a benzimidazole group, a benzothiazole group, a benzocarbazole group, a benzothiophene group, a dibenzothiophene group, a benzofuran group, a phenanthroline group, an isoxazole group, a thiadiazole group, a dibenzofuran group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups can include monocyclic heteroaryl groups, polycyclic heteroaryl groups, or both monocyclic heteroaryl groups and polycyclic heteroaryl groups. For example, the heteroaryl group in the heteroarylamine group can be selected from among the examples of the heteroaryl group described above.

In the present specification, the meaning of "adjacent two of substituents bonding to each other to form a ring" means bonding to adjacent groups to form a substituted or unsubstituted hydrocarbon ring; or a substituted or unsubstituted heteroring.

In the present specification, the "ring" in the substituted or unsubstituted ring formed by bonding to each other means a substituted or unsubstituted hydrocarbon ring; or a substituted or unsubstituted heteroring.

In the present specification, the hydrocarbon ring can be an aromatic hydrocarbon ring, an aliphatic hydrocarbon ring, or a fused ring of aromatic hydrocarbon and aliphatic hydrocarbon, and can be selected from among the examples of the cycloalkyl group or the aryl group except for those that are not monovalent.

In the present specification, the heteroring means a ring including one or more atoms that are not carbon, that is, heteroatoms, and specifically, the heteroatom can include one or more atoms selected form the group consisting of O, N, Se, S and the like. The heteroring can be monocyclic or polycyclic, and can be an aromatic ring, aliphatic ring, or a fused ring of an aromatic ring and aliphatic ring. The aromatic heteroring can be selected from among the examples of the heteroaryl group except for those that are not monovalent.

In the present specification, the aliphatic heteroring means an aliphatic ring including one or more of heteroatoms. Examples of the aliphatic heteroring can include oxirane, tetrahydrofuran, 1,4-dioxane, pyrrolidine, piperidine, morpholine, oxepane, azokane, thiokane, and the like, but are not limited thereto.

In the present specification, the arylene group means the aryl group having two bonding sites, that is, a divalent group. The descriptions of the aryl group provided above can be applied thereto except that these are each a divalent group.

In the present specification, the heteroarylene group means the heteroaryl group having two bonding sites, that is, a divalent group. The descriptions of the heteroaryl group provided above can be applied thereto except that these are each a divalent group.

In one embodiment of the present specification, L is a direct bond, a substituted or unsubstituted arylene group having 6 to 30 carbon atoms, or a substituted or unsubstituted heteroarylene group having 2 to 30 carbon atoms.

In one embodiment of the present specification, L is a direct bond; a substituted or unsubstituted arylene group having 6 to 20 carbon atoms, or a substituted or unsubstituted heteroarylene group having 2 to 20 carbon atoms.

In one embodiment of the present specification, L is a direct bond; an arylene group having 6 to 20 carbon atoms that is unsubstituted or substituted with an alkyl group, a cycloalkyl group or an aryl group; or a heteroarylene group having 2 to 20 carbon atoms.

In one embodiment of the present specification, L is a direct bond, a substituted or unsubstituted phenylene group, a substituted or unsubstituted naphthylene group, a substituted or unsubstituted biphenylylene group, a substituted or unsubstituted divalent phenanthrene group, a substituted or unsubstituted divalent phenalene group, a substituted or unsubstituted divalent pyrene group, a substituted or unsubstituted divalent fluoranthene group, a substituted or unsubstituted divalent fluorenyl group, a substituted or unsubstituted divalent pyridine group, a substituted or unsubstituted divalent pyridazine group, a substituted or unsubstituted divalent carbazole group, a substituted or unsubstituted divalent dibenzothiophene group, a substituted or unsubstituted divalent t-benzothiophene group, or a substituted or unsubstituted divalent quinazoline group.

In one embodiment of the present specification, L is a direct bond; a phenylene group; a naphthylene group; a biphenylylene group; a divalent phenanthrene group; a divalent phenalene group; a divalent pyrene group; a divalent fluoranthene group; a divalent fluorenyl group substituted with an alkyl group; a divalent spiriocyclohexanefluorenyl group; a divalent pyridine group; a divalent pyridazine group; a divalent carbazole group; a divalent dibenzothiophene group; a divalent t-benzothiophene group; or a divalent quinazoline group.

In one embodiment of the present specification, L is a direct bond, a phenylene group, a naphthylene group, a biphenylylene group, a divalent phenanthrene group, a divalent phenalene group, a divalent pyrene group, a divalent fluoranthene group, a divalent dimethylfluorenyl group, a divalent spirocyclohexanefluorene group, a divalent pyridine group, a divalent pyridazine group, a divalent carbazole group, a divalent dibenzothiophene group, a divalent t-benzothiophene group, or a divalent quinazoline group.

In one embodiment of the present specification, n is 1 or 2.

In one embodiment of the present specification, n is 1.

In one embodiment of the present specification, n is 2.

In one embodiment of the present specification, r2 is an integer of 0 to 4, and when r2 is 2 or greater, the R2s are the same as or different from each other.

In one embodiment of the present specification, r3 is an integer of 0 to 6, and when r3 is 2 or greater, the R3s are the same as or different from each other.

In one embodiment of the present specification, R1 is a substituted or unsubstituted alkyl group.

In one embodiment of the present specification, R1 is a substituted or unsubstituted alkyl group having 1 to 20 carbon atoms.

In one embodiment of the present specification, R1 is a substituted or unsubstituted alkyl group having 1 to 10 carbon atoms.

In one embodiment of the present specification, R1 is a substituted or unsubstituted alkyl group having 2 to 10 carbon atoms.

In one embodiment of the present specification, R1 is an alkyl group having 1 to 20 carbon atoms.

In one embodiment of the present specification, R1 is an alkyl group having 1 to 10 carbon atoms.

In one embodiment of the present specification, R1 is an alkyl group having 2 to 10 carbon atoms.

In one embodiment of the present specification, R2 is hydrogen, deuterium, a substituted or unsubstituted alkyl group, or a substituted or unsubstituted aryl group.

In one embodiment of the present specification, R2 is hydrogen, deuterium, or a substituted or unsubstituted aryl group.

In one embodiment of the present specification, R2 is hydrogen, deuterium, or a substituted or unsubstituted aryl group having 6 to 20 carbon atoms.

In one embodiment of the present specification, R2 is hydrogen, deuterium, or an aryl group having 6 to 20 carbon atoms.

In one embodiment of the present specification, R2 is hydrogen, deuterium or a phenyl group.

In one embodiment of the present specification, R3 is hydrogen, deuterium, a substituted or unsubstituted alkyl group, or a substituted or unsubstituted aryl group.

In one embodiment of the present specification, R3 is hydrogen or deuterium.

In one embodiment of the present specification, R3 is hydrogen.

In one embodiment of the present specification, R4 is hydrogen, deuterium, or a substituted or unsubstituted alkyl group.

In one embodiment of the present specification, R4 is hydrogen, deuterium, or an alkyl group having 1 to 10 carbon atoms.

In one embodiment of the present specification, R4 is hydrogen or deuterium.

In one embodiment of the present specification, Ar1 and Ar2 are the same as or different from each other, and are each independently a substituted or unsubstituted aryl group.

In one embodiment of the present specification, Ar1 and Ar2 are the same as or different from each other, and are each independently a substituted or unsubstituted aryl group having 6 to 30 carbon atoms.

In one embodiment of the present specification, Ar1 and Ar2 are the same as or different from each other, and are each independently a substituted or unsubstituted aryl group having 6 to 20 carbon atoms.

In one embodiment of the present specification, Ar1 and Ar2 are the same as or different from each other, and are each independently is an aryl group that is unsubstituted or substituted with one or more substituents selected from the group consisting of an alkyl group, an alkoxy group, an aryl group and a heteroaryl group.

In one embodiment of the present specification, Ar1 and Ar2 are the same as or different from each other, and are each independently a substituted or unsubstituted phenyl group, or a substituted or unsubstituted naphthyl group.

In one embodiment of the present specification, Ar1 and Ar2 are the same as or different from each other, and are each independently a phenyl group that is unsubstituted or substituted with one or more substituents selected from the group consisting of an alkyl group, an alkoxy group, an aryl group and a heteroaryl group; or a naphthyl group that is unsubstituted or substituted with one or more substituents selected from the group consisting of an alkyl group, an alkoxy group, an aryl group and a heteroaryl group.

In one embodiment of the present specification, Ar1 and Ar2 are the same as or different from each other, and are each independently a phenyl group; a naphthyl group; a phenyl group substituted with an alkyl group; a phenyl group substituted with an aryl group; a phenyl group substituted with a heteroaryl group; a phenyl group substituted with an alkoxy group; or a phenyl group substituted with a heteroaryl group substituted with an aryl group.

In one embodiment of the present specification, Ar1 and Ar2 are the same as or different from each other, and are each independently a phenyl group that is unsubstituted or substituted with one or more substituents selected from the group consisting of an alkyl group having 1 to 5 carbon atoms, a pyridine group, a pyrimidine group, a triazine group, a methoxy group and a phenyl group; or a naphthyl group.

In one embodiment of the present specification, Ar1 and Ar2 are the same as or different from each other, and are each independently a phenyl group; a naphthyl group; a phenyl group substituted with a butyl group; a phenyl group substituted with a pyridine group; a phenyl group substituted with a methoxy group; a phenyl group substituted with a diphenyltriazine group; or a phenyl group substituted with a diphenylpyrimidine group.

In one embodiment of the present specification, the compound of Chemical Formula 1 is any one compound selected from among the following compounds:

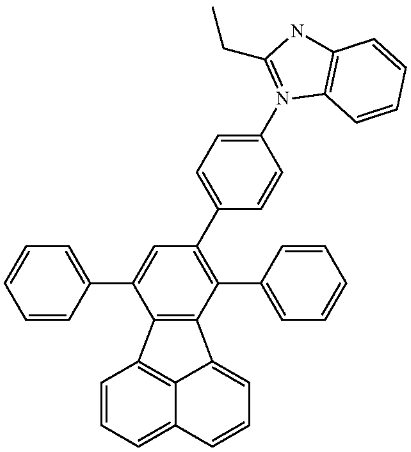
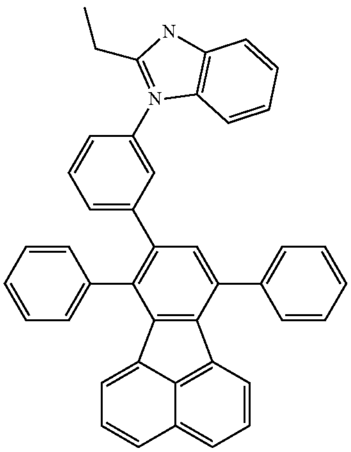
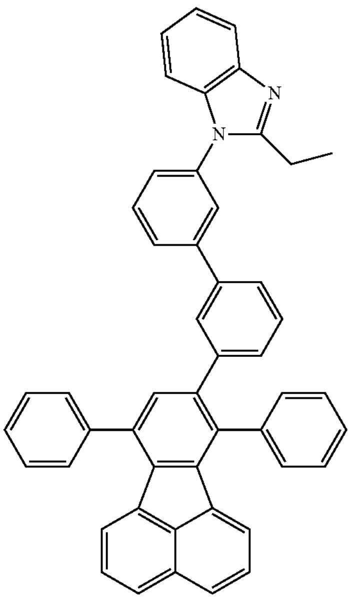
-continued
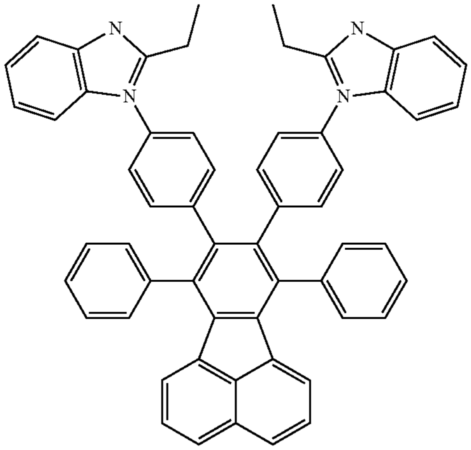
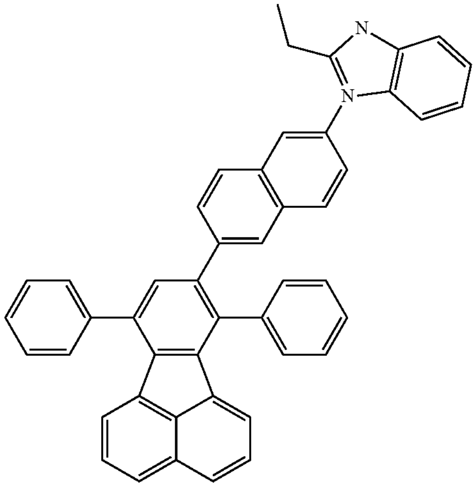
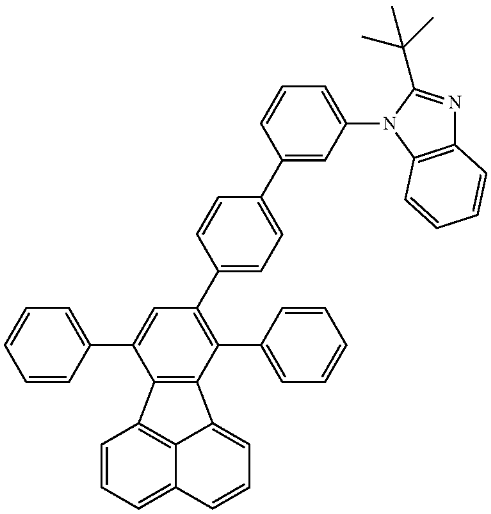

-continued
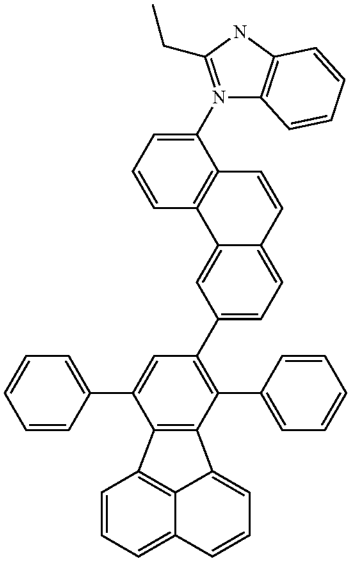
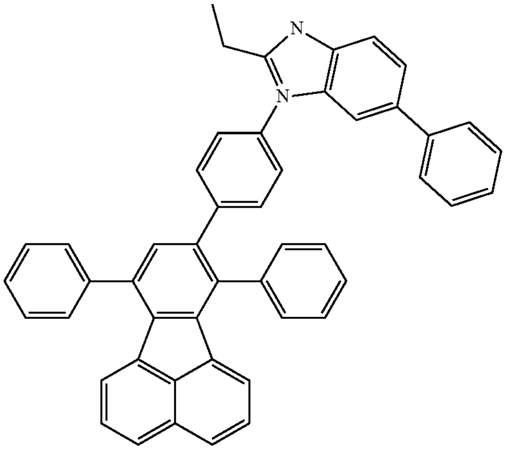
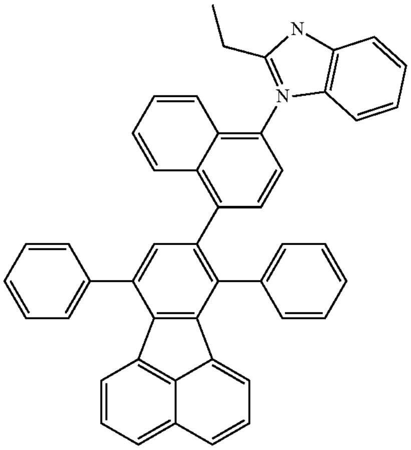
-continued
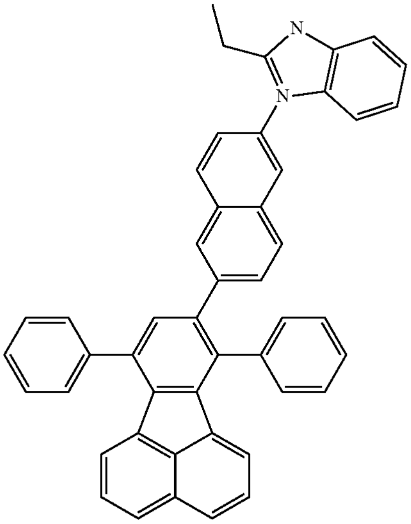
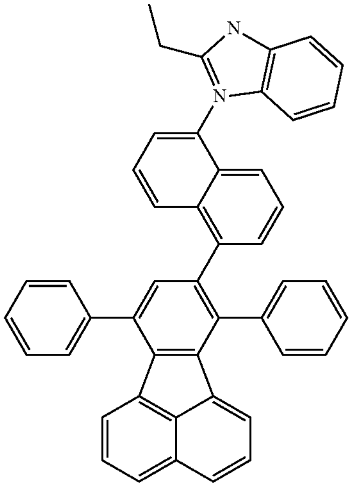
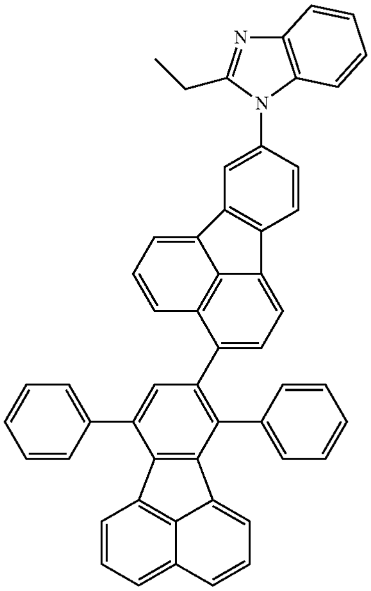

-continued
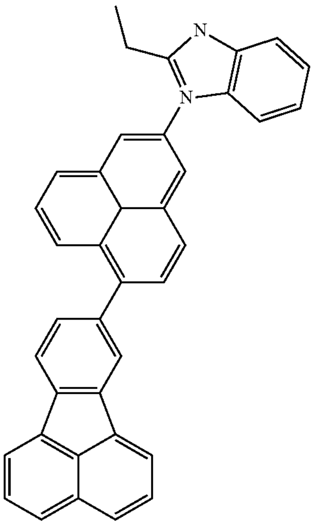
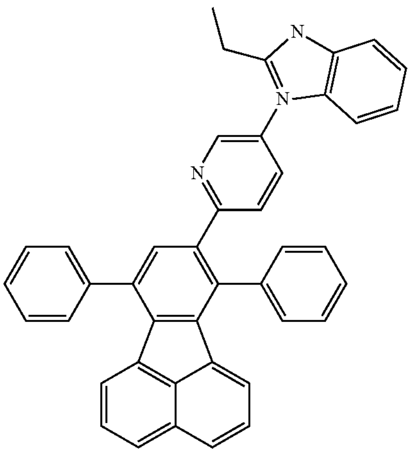
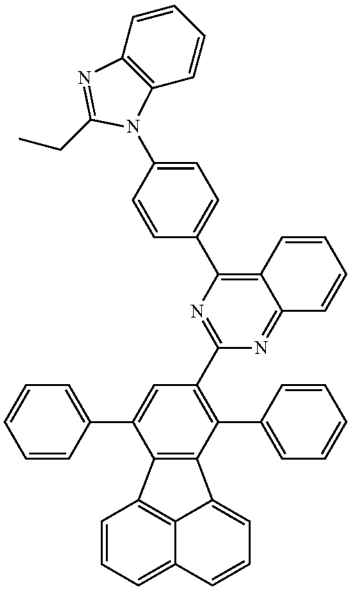
-continued
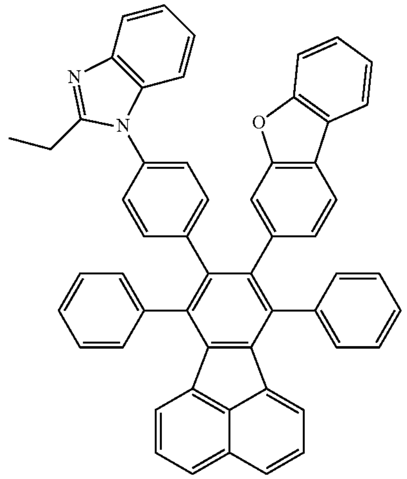
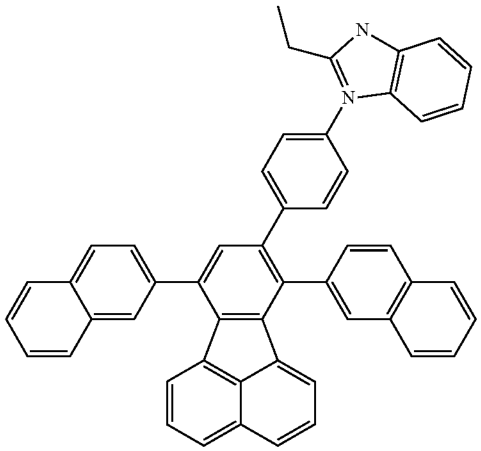
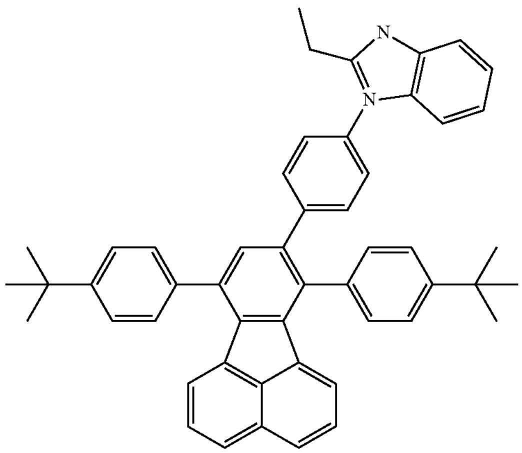

-continued
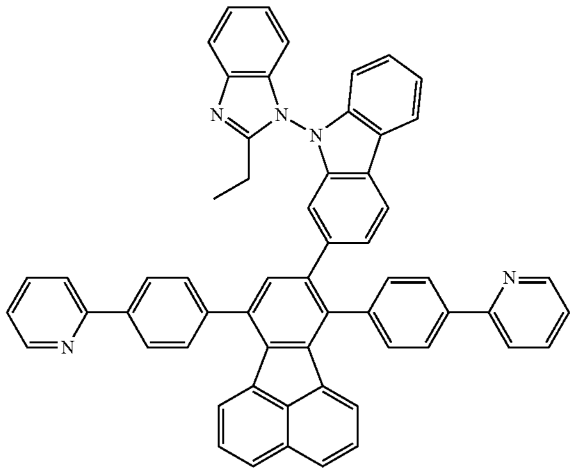
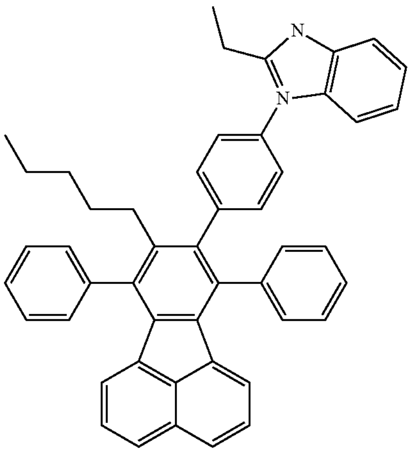
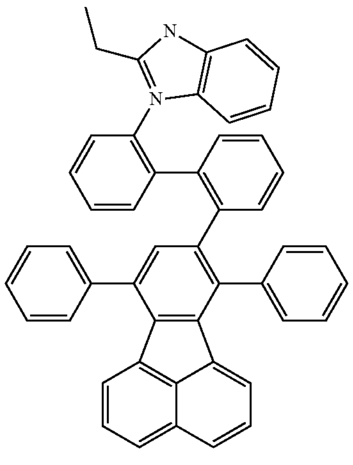
-continued
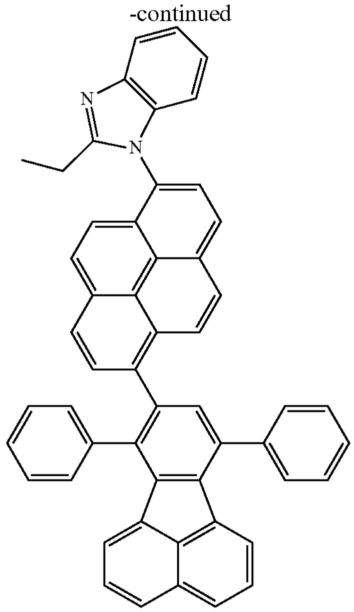
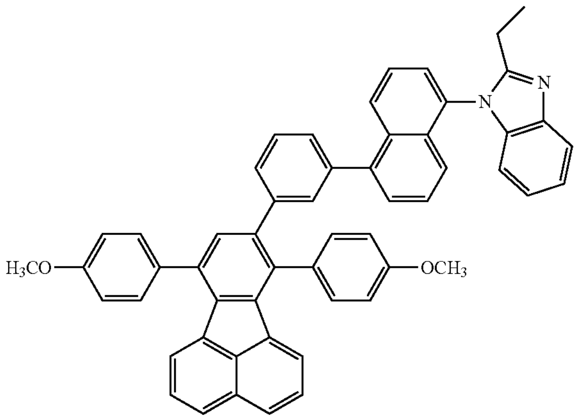
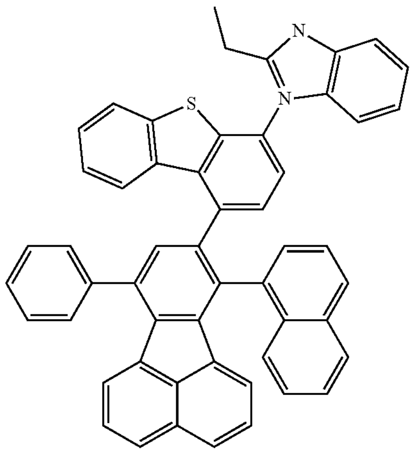

-continued
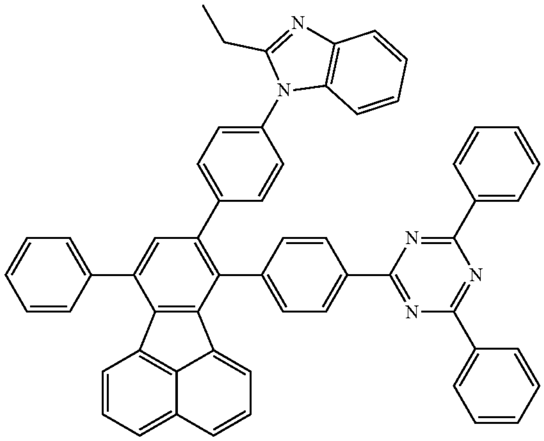
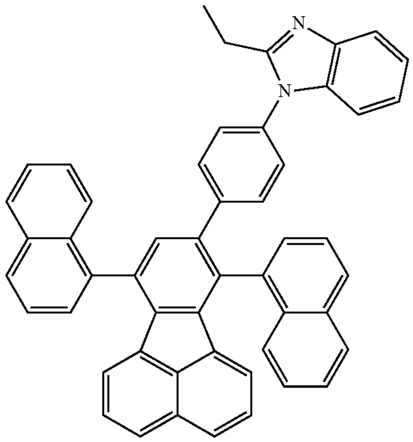
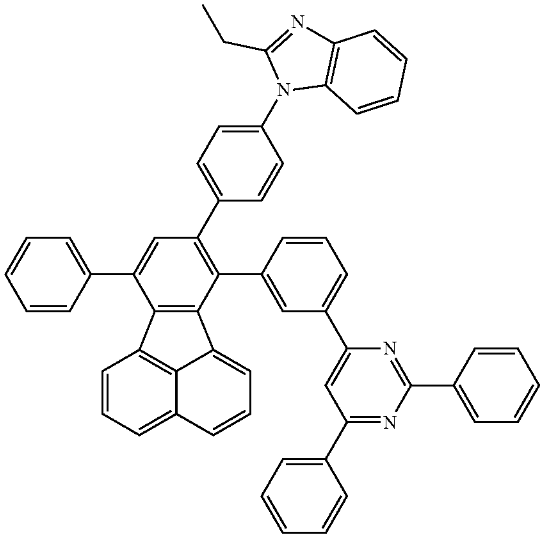
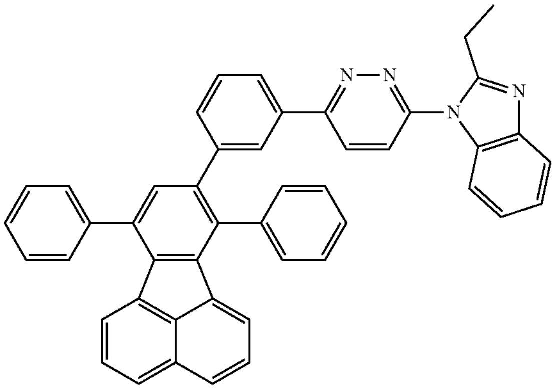
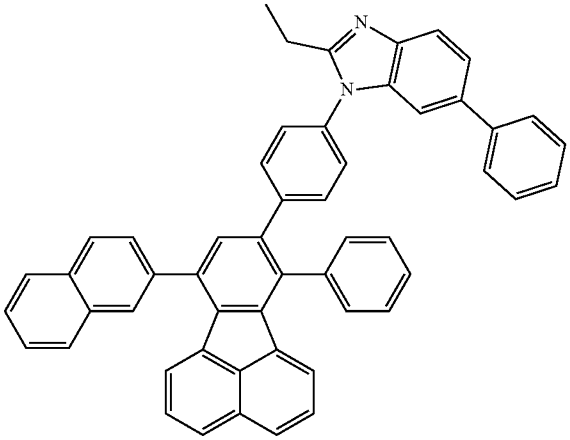
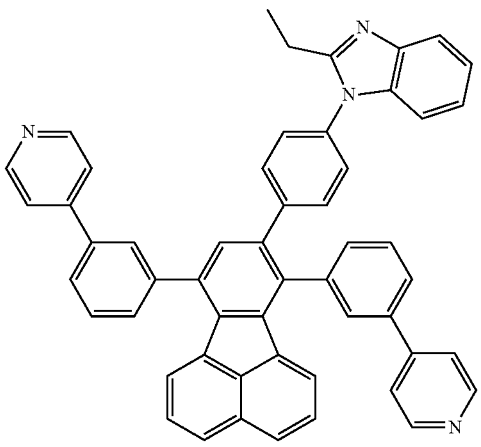

-continued

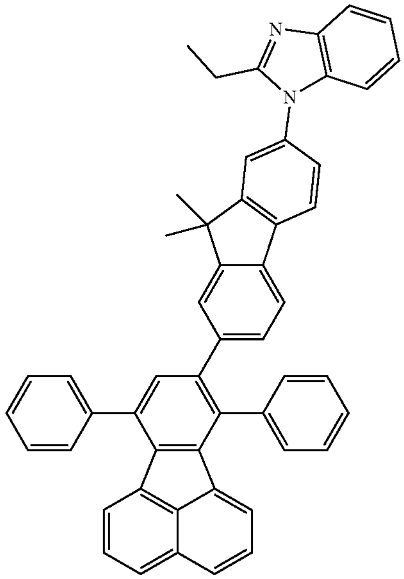

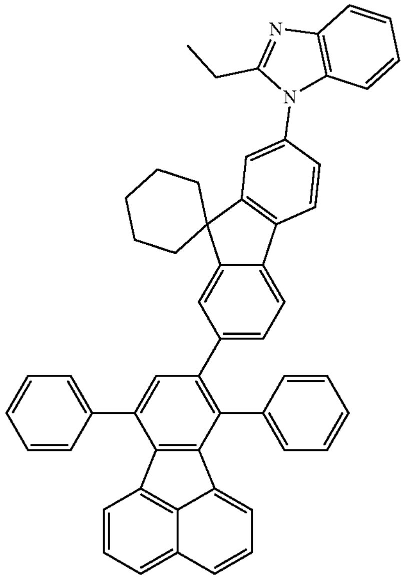

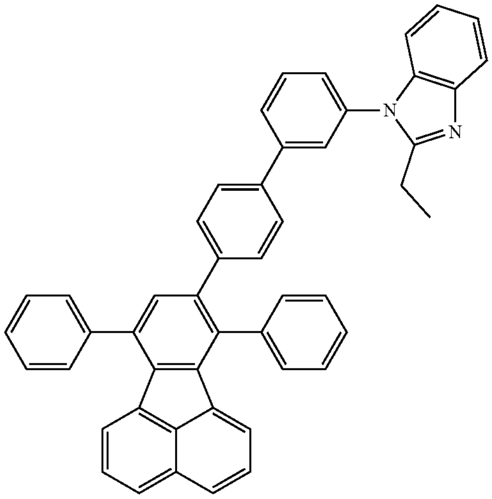

-continued

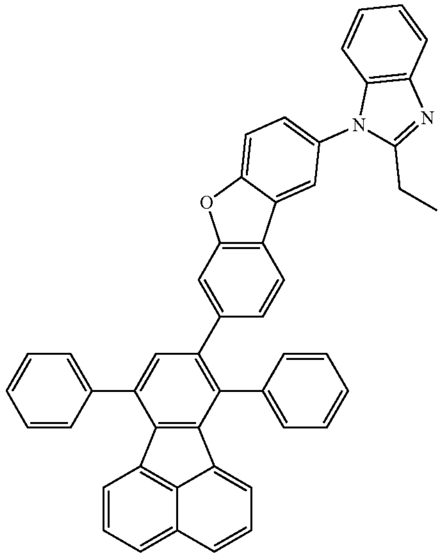

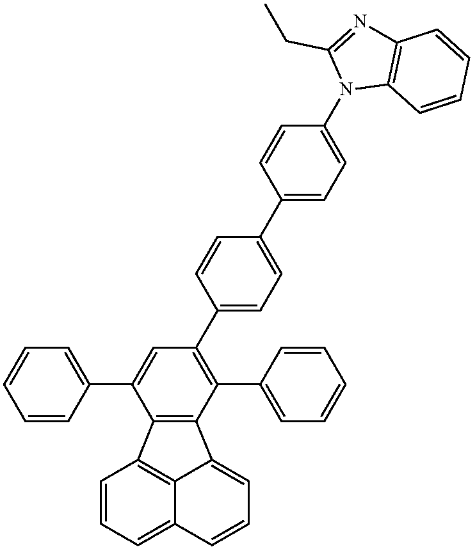

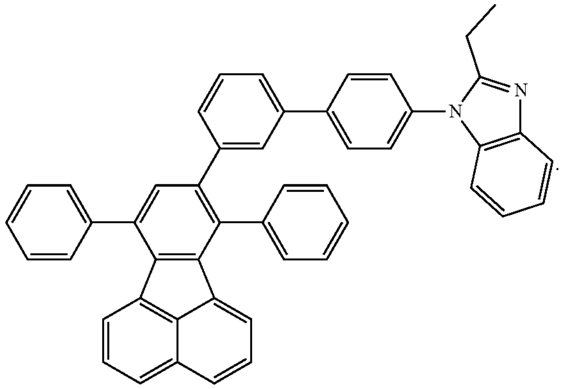

In addition, one embodiment of the present specification provides an organic light emitting device including the compound described above.

One embodiment of the present application provides an organic light emitting device including a first electrode; a second electrode opposite to the first electrode; and one or more organic material layers between the first electrode and the second electrode, wherein one or more layers of the organic material layers include the compound described above.

For example, the organic light emitting device of the present disclosure can have a structure as illustrated in FIG. 1, however, the structure is not limited thereto.

FIG. 1 illustrates a structure of the organic light emitting device in which a first electrode (2), an organic material layer (3) and a second electrode (4) are consecutively laminated on a substrate (1).

FIG. 2 illustrates a structure of the organic light emitting device in which a substrate (1), a first electrode (2), a hole injection layer (5), a first hole transfer layer (6), a second hole transfer layer (7), a light emitting layer (8), an electron injection and transfer layer (9) and a second electrode (4) are consecutively laminated.

FIG. 1 and FIG. 2 illustrate the organic light emitting device, and the structure is not limited thereto. The organic material layer of the organic light emitting device of the present application can be formed in a single layer structure, but can also be formed in a multilayer structure in which two or more organic material layers are laminated. For example, typical examples of the organic light emitting device of the present disclosure can have a structure including a hole injection layer, a hole transfer layer, a light emitting layer, an electron transfer layer, an electron injection layer and the like as the organic material layer. However, the structure of the organic light emitting device is not limited thereto, and can include a smaller number of organic material layers.

In one embodiment of the present application, the organic material layer includes a light emitting layer, and the light emitting layer includes the compound.

In one embodiment of the present application, the organic material layer includes a hole injection layer or a hole transfer layer, and the hole injection layer or the hole transfer layer includes the compound.

In one embodiment of the present application, the organic material layer includes a hole injection layer, a hole transfer layer, or a hole injection and transfer layer, and the hole injection layer, the hole transfer layer, or the hole injection and transfer layer includes the compound.

In one embodiment of the present application, the organic material layer includes an electron transfer layer or an electron injection layer, and the electron transfer layer or the electron injection layer includes the compound.

In one embodiment of the present application, the organic material layer includes a hole blocking layer, an electron injection layer, an electron transfer layer, or an electron injection and transfer layer, and the hole blocking layer, the electron injection layer, the electron transfer layer, or the electron injection and transfer layer includes the compound.

In one embodiment of the present application, the hole blocking layer, the electron injection layer, the electron transfer layer, or the electron injection and transfer layer includes the compound and a metal complex compound.

In one embodiment of the present application, the hole blocking layer, the electron injection layer, the electron transfer layer, or the electron injection and transfer layer is positioned in contact with the light emitting layer.

In one embodiment of the present application, the compound and the metal complex compound are included in a weight ratio of 1:9 to 9:1, and specifically, can be included in a weight ratio of 3:7 to 7:3.

In one embodiment of the present application, the metal complex compound can be a metal complex compound to describe below, and although LiQ (lithium quinolate) can be used, the metal complex compound is not limited thereto.

In one embodiment of the present disclosure, the organic material layer can include a hole injection layer, a first hole transfer layer, a second hole transfer layer, a light emitting layer, or an electron injection and transfer layer.

In one embodiment of the present disclosure, the organic material layer includes a light emitting layer, and the light emitting layer can be, but is not limited to, a blue light emitting layer, a red light emitting layer or a green light emitting layer.

In one embodiment of the present disclosure, the organic material layer includes a light emitting layer, and the light emitting layer is a blue light emitting layer.

In one embodiment of the present disclosure, the organic material layer includes a light emitting layer, and the light emitting layer includes a blue dopant and a blue host.

In one embodiment of the present disclosure, the organic material layer includes a light emitting layer, and the light emitting layer can include a host and a dopant in a weight ratio of 100:1 to 1:1, and can specifically include a host and a dopant in a weight ratio of 99:1 to 10:1.

In one embodiment of the present disclosure, the organic material layer includes a light emitting layer, and the light emitting layer includes a host and a dopant in a weight ratio of 25:1.

In one embodiment of the present disclosure, the organic material layer includes a light emitting layer, and the light emitting layer includes a host material.

In one embodiment of the present disclosure, the host material is an anthracene-based compound.

In one embodiment of the present disclosure, the host material can be of the following Chemical Formula H:

[Chemical Formula H]

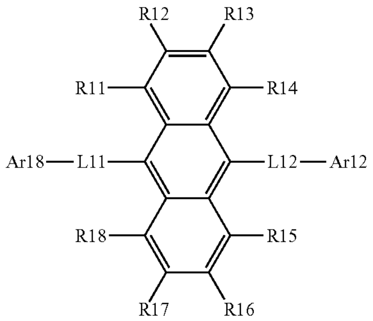

wherein in Chemical Formula H:

R11 to R18 are the same as or different from each other, and are each independently hydrogen, deuterium, a halogen group, a substituted or unsubstituted alkyl group, —$OR_{21}$, a substituted or unsubstituted aryl group, —$NR_{22}R_{23}$, —$SiR_{24}R_{25}$—O—$SiR_{26}R_{27}R_{28}$, or —$SiR_{29}R_{30}R_{31}$;

$R_{21}$ to $R_{31}$ are the same as or different from each other, and are each independently hydrogen, deuterium, a substituted or unsubstituted alkyl group, or a substituted or unsubstituted aryl group;

L11 and L12 are the same as or different from each other, and are each independently a direct bond, a substituted or unsubstituted arylene group, or a substituted or unsubstituted heteroarylene group; and Ar11 and Ar12 are the same as or different from each other, and are each independently hydrogen, deuterium, a substituted or unsubstituted aryl group, or a substituted or unsubstituted heteroaryl group.

In one embodiment of the present disclosure, R11 to R18 are the same as or different from each other, and are each independently hydrogen or deuterium.

In one embodiment of the present disclosure, at least one of R11 to R18 is deuterium.

In one embodiment of the present disclosure, at least one of L11 and L12 is substituted with deuterium.

In one embodiment of the present disclosure, at least one of Ar1 and Ar2 is substituted with deuterium.

In one embodiment of the present specification, the compound of Chemical Formula H is 0% to 100% deuterated.

In one embodiment of the present specification, the compound of Chemical Formula H is 10% to 100% deuterated.

In one embodiment of the present specification, the compound of Chemical Formula H is 40% to 100% deuterated.

In one embodiment of the present specification, the compound of Chemical Formula H is 50% to 100% deuterated.

The term "deuterated" intends to mean that at least one available H is replaced by D. In an X % deuterated compound or group, X % of available H is replaced by D. A deuterated compound or group has deuterium present in 100 times or higher of the natural abundance level.

In one embodiment of the present specification, when the compound of Chemical Formula H is deuterated, chemical properties of the compound hardly change. However, since the atomic weight of deuterium is twice the atomic weight of hydrogen, the deuterated compound can have physical properties changed. As one example, the compound substituted with deuterium has a decreased vibrational energy level. The compound substituted with deuterium can prevent a decrease in the Van der Waals force between molecules or a decrease in the quantum efficiency resulting from collisions caused by vibrations between molecules. In addition, bonding between carbon and deuterium (C-D) can improve stability of the compound. Accordingly, efficiency and lifetime of a device can be improved when the compound of Chemical Formula H is deuterated.

Particularly, when at least one of R11 to R18 includes deuterium, stability for the whole material is favorable compared to when R11 to R18 are hydrogen. In addition, as the number of deuterium increases, energy required for side reactions increases making it difficult to generate side reactions, and as a result, stability of the compound significantly increases.

In one embodiment of the present disclosure, L11 and L12 are the same as or different from each other, and are each independently a direct bond or an arylene group.

In one embodiment of the present disclosure, L11 and L12 are the same as or different from each other, and are each independently a direct bond, a phenylene group, a biphenylylene group, or a naphthylene group.

In one embodiment of the present disclosure, L11 and L12 are a direct bond.

In one embodiment of the present disclosure, Ar11 and Ar12 are the same as or different from each other, and are each independently a substituted or unsubstituted aryl group or a substituted or unsubstituted heteroaryl group.

In one embodiment of the present disclosure, Ar11 and Ar12 are the same as or different from each other, and are each independently is an aryl group having 6 to 30 carbon atoms, or a heteroaryl group having 2 to 20 carbon atoms.

In one embodiment of the present disclosure, Ar11 and Ar12 are the same as or different from each other, and are each independently a phenyl group, a biphenyl group, a naphthyl group, a dibenzofuran group, or a dibenzothiophene group.

In one embodiment of the present disclosure, the organic material layer includes a light emitting layer, and the light emitting layer includes a dopant material.

In one embodiment of the present disclosure, the dopant material is a compound including boron.

In one embodiment of the present disclosure, the dopant material can be the following Chemical Formula D:

[Chemical Formula D]

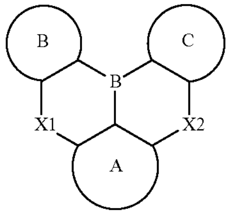

wherein in Chemical Formula D:

A, B and C are the same as or different from each other, and are each independently a substituted or unsubstituted hydrocarbon ring or a substituted or unsubstituted heteroring;

X1 and X2 are the same as or different from each other, and are each independently O, $CR_{40}R_{41}$ or $NR_{42}$;

$R_{40}$ to $R_{42}$ are the same as or different from each other, and are each independently hydrogen, deuterium, a halogen group, a cyano group, a substituted or unsubstituted alkyl group, a substituted or unsubstituted silyl group, a substituted or unsubstituted alkoxy group, a substituted or unsubstituted aryl group, or a substituted or unsubstituted heterocyclic group; and adjacent groups among $R_{40}$ to $R_{42}$, A, B and C can bond to each other to form a substituted or unsubstituted ring.

In one embodiment of the present application, A, B and C are a substituted or unsubstituted aromatic ring.

In one embodiment of the present application, A, B and C are a substituted or unsubstituted benzene ring.

In one embodiment of the present application, A, B and C are a benzene ring that is unsubstituted or substituted with an alkyl group or an amine group.

In one embodiment of the present application, A, B and C are a benzene ring that is unsubstituted or substituted with an alkyl group.

In one embodiment of the present application, X1 and X2 are $NR_{42}$.

In one embodiment of the present application, $R_{42}$ is a substituted or unsubstituted alkyl group, a substituted or unsubstituted aryl group, or a substituted or unsubstituted heterocyclic group.

In one embodiment of the present application, $R_{42}$ is a substituted or unsubstituted aryl group or a substituted or unsubstituted heterocyclic group.

In one embodiment of the present application, $R_{42}$ is a substituted or unsubstituted aryl group.

In one embodiment of the present application, $R_{42}$ is an aryl group that is unsubstituted or substituted with an alkyl group.

In one embodiment of the present application, $R_{42}$ is a substituted or unsubstituted phenyl group.

In one embodiment of the present application, $R_{42}$ is a phenyl group that is unsubstituted or substituted with an alkyl group.

In one embodiment of the present application, the organic material layer includes a hole injection layer, a hole transfer layer, or a hole injection and transfer layer, and the hole injection layer, the hole transfer layer, or the hole injection and transfer layer includes an amine-based compound.

For example, the organic light emitting device of the present application can be manufactured by consecutively laminating a first electrode, an organic material layer and a second electrode on a substrate. Herein, the organic light emitting device can be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer and an electron transfer layer thereon, and then depositing a material usable as a cathode thereon. In addition to such a method, the organic light emitting device can also be manufactured by consecutively depositing a cathode material, an organic material layer and an anode material on a substrate.

In addition, the compound of Chemical Formula 1 can be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In one embodiment of the present application, the first electrode is an anode, and the second electrode is a cathode.

In another embodiment, the first electrode is a cathode, and the second electrode is an anode.

The anode is an electrode injecting holes, and as the anode material, materials having large work function are normally preferred so that hole injection to an organic material layer is smooth. Specific examples of the anode material that can be used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

The cathode is an electrode injecting electrons, and as the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer performing a role of smoothly injecting holes from an anode to a light emitting layer, and the hole injection material is a material capable of favorably receiving holes from an anode at a low voltage. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto. The hole injection layer can have a thickness of 1 nm to 150 nm. The hole injection layer having a thickness of 1 nm or greater has an advantage of preventing hole injection properties from declining, and the thickness being 150 nm or less has an advantage of preventing a driving voltage from increasing to enhance hole migration caused by the hole injection layer being too thick.

The hole transfer layer can perform a role of smoothly transferring holes. As the hole transfer material, materials capable of receiving holes from an anode or a hole injection layer, moving the holes to a light emitting layer, and having high mobility for the holes are suited. Specific examples thereof include arylamine-based organic materials, conductive polymers, block copolymers having conjugated parts and non-conjugated parts together, and the like, but are not limited thereto.

An electron blocking layer can be provided between the hole transfer layer and a light emitting layer. As the electron blocking layer, materials known in the art can be used.

The light emitting layer can emit red, green or blue light, and can be formed with a phosphorescence material or a fluorescence material. The light emitting material is a material capable of emitting light in a visible region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

A host material of the light emitting layer can include fused aromatic ring derivatives, heteroring-containing compounds or the like. Specifically, as the fused aromatic ring derivative, anthracene derivatives, pyrene derivatives, naphthalene derivatives, pentacene derivatives, phenanthrene compounds, fluoranthene compounds and the like can be included, and as the heteroring-containing compound, carbazole derivatives, dibenzofuran derivatives, ladder-type furan compounds, pyrimidine derivatives and the like can be included, however, the host material is not limited thereto.

When the light emitting layer emits red light, phosphorescence materials such as PIQIr(acac) (bis(1-phenylisoquinoline) acetylacetonate iridium), PQIr(acac) (bis(1-phenylquinoline)acetylacetonate iridium), PQIr (tris(1-phenylquinoline)iridium) or PtOEP (octaethylporphyrin platinum), or fluorescence materials such as $Alq_3$ (tris(8-hydroxyquinolino)aluminum) can be used as the light emitting dopant, however, the light emitting dopant is not limited thereto. When the light emitting layer emits green light, phosphorescence materials such as $Ir(ppy)_3$ (fac tris(2-phenylpyridine)iridium), or fluorescence materials such as $Alq_3$ (tris(8-hydroxyquinolino)aluminum), anthracene-based compounds, pyrene-based compounds or boron-based compounds can be used as the light emitting dopant, however, the light emitting dopant is not limited thereto. When the light emitting layer emits blue light, phosphorescence materials such as $(4,6\text{-}F_2ppy)_2Irpic$, or fluorescence materials such as spiro-DPVBi, spiro-6P, distyrylbenzene (DSB), distyrylarylene (DSA), PFO-based polymers, PPV-based polymers, anthracene-based compounds, pyrene-based compounds or boron-based compounds can be used as the light emitting dopant, however, the light emitting dopant is not limited thereto.

The electron transfer layer can perform a role of smoothly transferring electrons. As the electron transfer material, materials capable of favorably receiving electrons from a cathode, moving the electrons to a light emitting layer, and having high mobility for the electrons are suited. Specific examples thereof include Al complexes of 8-hydroxyquinoline; complexes including $Alq_3$; organic radical compounds; hydroxyflavon-metal complexes, and the like, but are not limited thereto. The electron transfer layer can have a thickness of 1 nm to 50 nm. The electron transfer layer having a thickness of 1 nm or greater has an advantage of preventing electron transfer properties from declining, and the thickness being 50 nm or less has an advantage of preventing a driving voltage from increasing to enhance electron migration caused by the electron transfer layer being too thick.

The electron injection layer can perform a role of smoothly injecting electrons. As the electron injection material, compounds having an electron transferring ability, having an electron injection effect from a cathode, having an excellent electron injection effect for a light emitting layer or light emitting material, and preventing excitons generated in the light emitting layer from moving to a hole injection layer, and, in addition thereto, having an excellent thin film forming ability are preferred. Specific examples thereof can include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

As the electron injection and transfer layer material, the material of the electron transfer layer or the material of the electron injection layer described above, or the like, can be included. In addition, the layer carrying out electron injection and transfer at the same time can further include a metal complex compound.

When the layer including Chemical Formula 1 of the present disclosure is an electron injection and transfer layer, the electron injection and transfer layer can be included in the electron injection and transfer layer including Chemical Formula 1, or can be included in an electron injection and transfer layer other than the electron injection and transfer layer including the compound of Chemical Formula 1.

When the organic light emitting device includes a plurality of organic material layers, the organic material layers can be formed with the same materials or different materials.

The metal complex compound includes 8-hydroxyquinolinato lithium, bis(8-hydroxyquinolinato)zinc, bis(8-hydroxyquinolinato)copper, bis(8-hydroxyquinolinato)-manganese, tris(8-hydroxyquinolinato)aluminum, tris(2-methyl-8-hydroxyquinolinato)aluminum, tris(8-hydroxyquinolinato)-gallium, bis(10-hydroxybenzo[h]quinolinato)beryllium, bis(10-hydroxybenzo[h]quinolinato)zinc, bis(2-methyl-8-quinolinato)-chlorogallium, bis(2-methyl-8-quinolinato) (o-cresolato)-gallium, bis(2-methyl-8-quinolinato)(1-naphtholato)aluminum, bis(2-methyl-8-quinolinato)(2-naphtholato)gallium and the like, but is not limited thereto.

The hole blocking layer is a layer blocking holes from reaching a cathode, and can be generally formed under the same condition as the hole injection layer. Specific examples thereof can include oxadiazole derivatives, triazole derivatives, phenanthroline derivatives, BCP, aluminum complexes and the like, but are not limited thereto.

The organic light emitting device according to the present disclosure can be a top-emission type, a bottom-emission type or a dual-emission type depending on the materials used.

Hereinafter, the present specification will be described in detail with reference to examples. However, the examples according to the present specification can be modified to various other forms, and the scope of the present application is not to be construed as being limited to the examples described below. Examples of the present application are provided in order to more fully describe the present specification to those having average knowledge in the art.

EXAMPLES

Synthesis Example

<Synthesis of Compound 1-1>

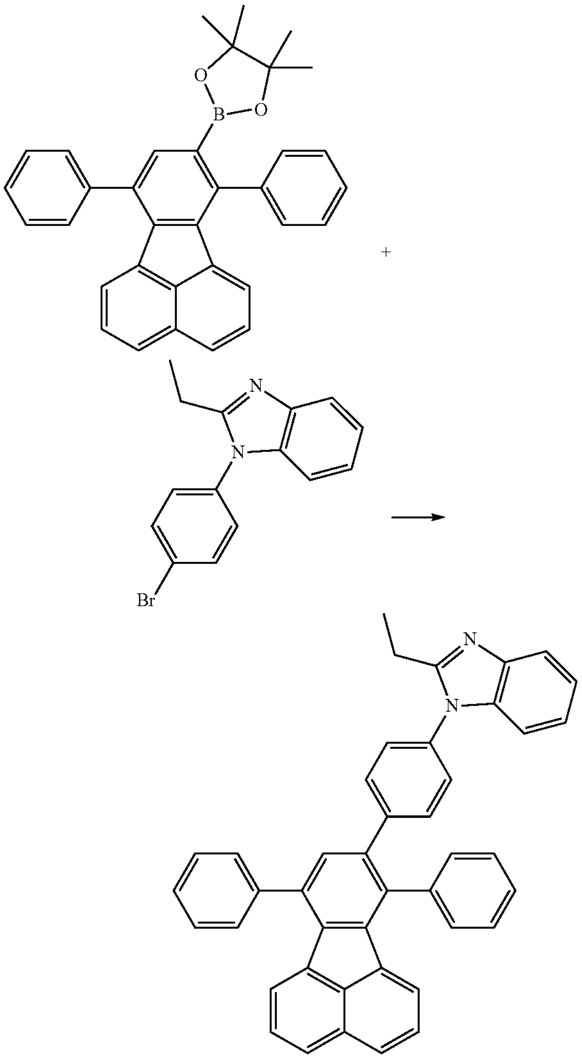

1-1

2-(7,10-Diphenylfluoranthen-8-yl)-4,4,5,5-tetramethyl-1,3,2-dioxaborolane (20 g, 41.63 mol), 1-(4-bromophenyl)-2-ethyl-1H-benzo[d]imidazole (12.54 g, 41.63 mmol) and an aqueous potassium carbonate (11.5 g, 83.26 mmol) solution were introduced to a tetrahydrofuran solvent (300 mL), and the temperature was raised. When the mixture started to reflux, tetrakis(triphenylphosphine)palladium(0) (1.44 g, 1.24 mmol) was introduced thereto, and the result was further stirred for an additional 1 hour. After terminating the reaction, the result was cooled and ethanol slurry purified to prepare [Compound 1-1] (21 g, yield 87.9%).

$[M+H]^+$=575

<Synthesis of Compound 1-2>

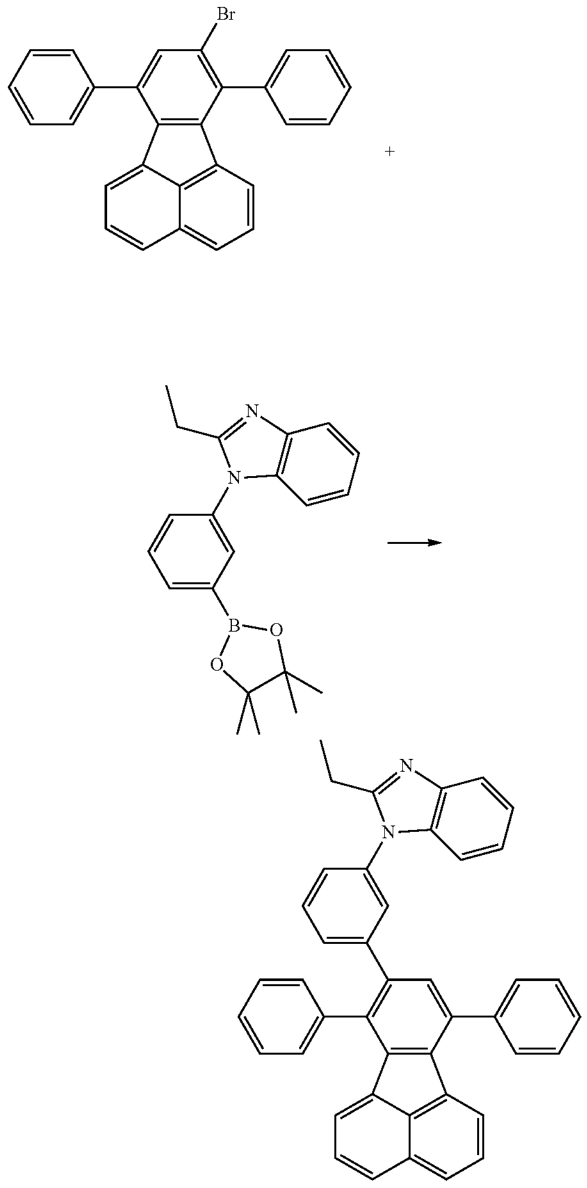

1-2

[Compound 1-2] was prepared in the same manner as in the synthesis method of [Compound 1-1] except that 8-bromo-7,10-diphenylfluoranthene was used instead of 2-(7,10-diphenylfluoranthen-8-yl)-4,4,5,5-tetramethyl-1,3,2-dioxaborolane, and 2-ethyl-1-(3-(4,4,5,5-tetramethyl-1,3,2-dioxaborolan-2-yl)phenyl)-1H-benzo[d]imidazole was used instead of 1-(4-bromophenyl)-2-ethyl-1H-benzo[d]imidazole.

$[M+H]^+$=575

<Synthesis of Compound 1-3>

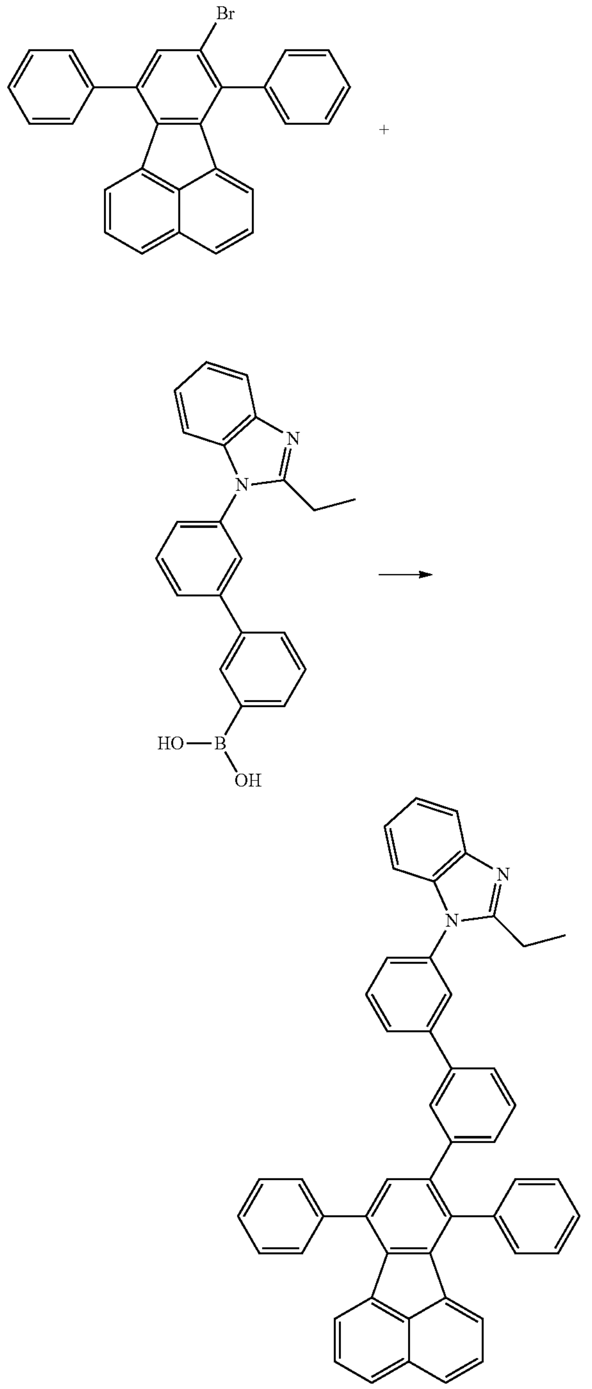

1-3

[Compound 1-3] was prepared in the same manner as in the synthesis method of [Compound 1-1] except that 8-bromo-7,10-diphenylfluoranthene was used instead of 2-(7,10-diphenylfluoranthen-8-yl)-4,4,5,5-tetramethyl-1,3,2-dioxaborolane, and (3'-(2-ethyl-1H-benzo[d]imidazol-1-yl)-[1,1'-biphenyl]-3-yl)boronic acid was used instead of 1-(4-bromophenyl)-2-ethyl-1H-benzo[d]imidazole.

$[M+H]^+$=651

<Synthesis of Compound 1-4>

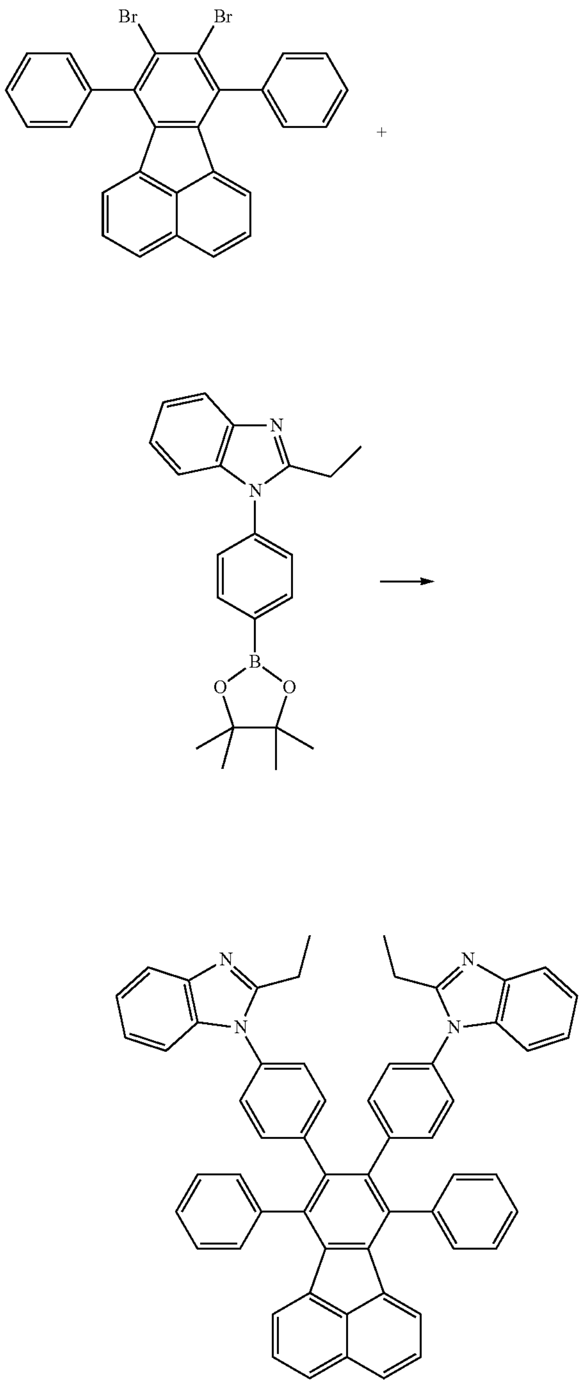

1-4

[Compound 1-4] was prepared in the same manner as in the synthesis method of [Compound 1-1] except that 8,9-dibromo-7,10-diphenylfluoranthene was used instead of 2-(7,10-diphenylfluoranthen-8-yl)-4,4,5,5-tetramethyl-1,3,2-dioxaborolane, and 2-ethyl-1-(4-(4,4,5,5-tetramethyl-1,3,2-dioxaborolan-2-yl)phenyl)-1H-benzo[d]imidazole was used instead of 1-(4-bromophenyl)-2-ethyl-1H-benzo[d]imidazole.

$[M+H]^+=795$

<Synthesis of Compound 1-5>

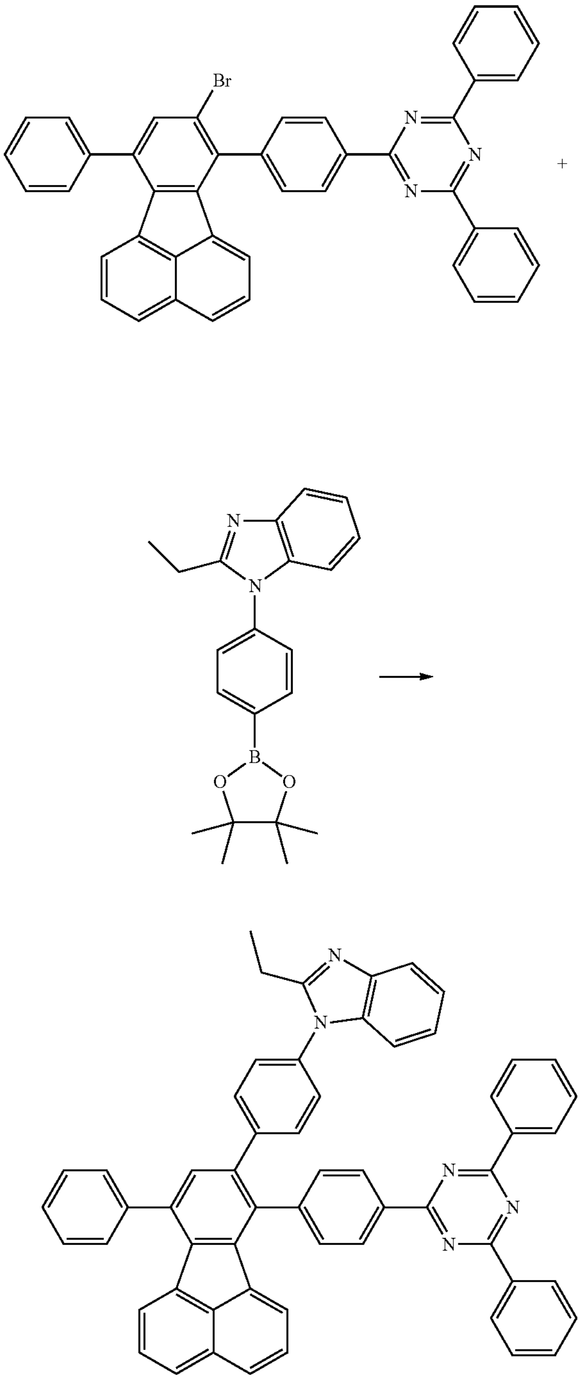

1-5

[Compound 1-5] was prepared in the same manner as in the synthesis method of [Compound 1-1] except that 2-(4-(8-bromo-10-phenylfluoranthen-7-yl)phenyl)-4,6-diphenyl-1,3,5-triazine was used instead of 2-(7,10-diphenylfluoranthen-8-yl)-4,4,5,5-tetramethyl-1,3,2-dioxaborolane, and 2-ethyl-1-(4-(4,4,5,5-tetramethyl-1,3,2-dioxaborolan-2-yl)phenyl)-1H-benzo[d]imidazole was used instead of 1-(4-bromophenyl)-2-ethyl-1H-benzo[d]imidazole.

$[M+H]^+=806$

<Synthesis of Compound 1-6>

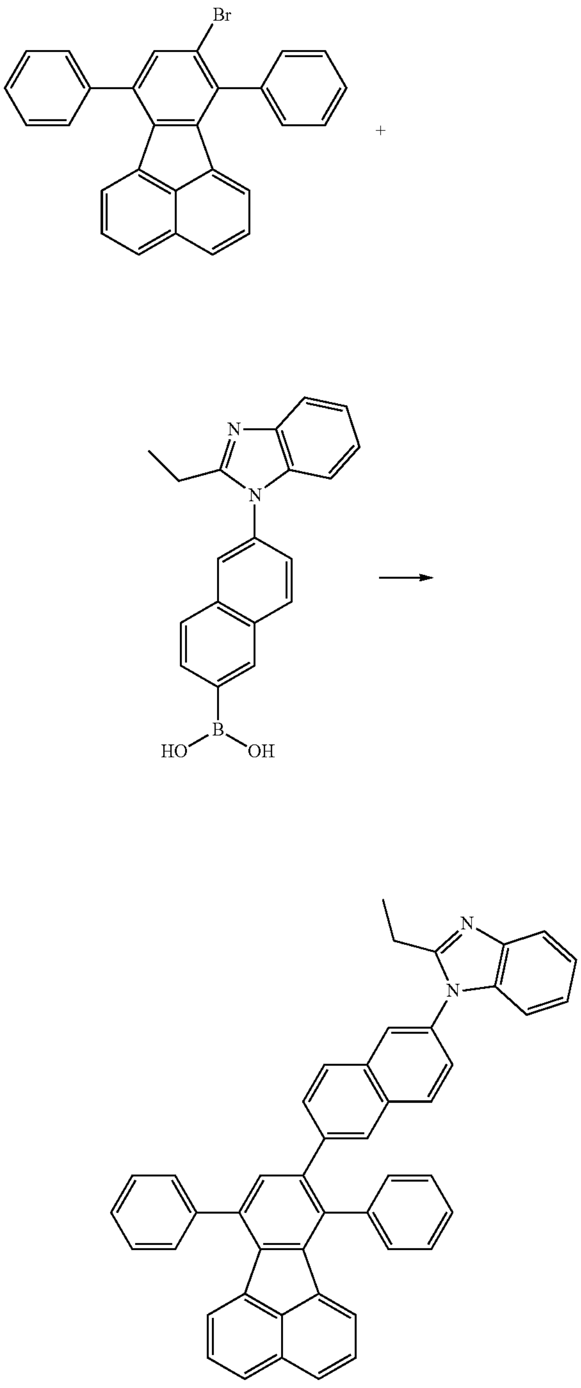

1-6

[Compound 1-6] was prepared in the same manner as in the synthesis method of [Compound 1-1] except that 8-bromo-7,10-diphenylfluoranthene was used instead of 2-(7,10-diphenylfluoranthen-8-yl)-4,4,5,5-tetramethyl-1,3,2-dioxaborolane, and (6-(2-ethyl-1H-benzo[d]imidazol-1-yl)naphthalen-2-yl)boronic acid was used instead of 1-(4-bromophenyl)-2-ethyl-1H-benzo[d]imidazole.

$[M+H]^+=625$

<Synthesis of Compound 1-7>

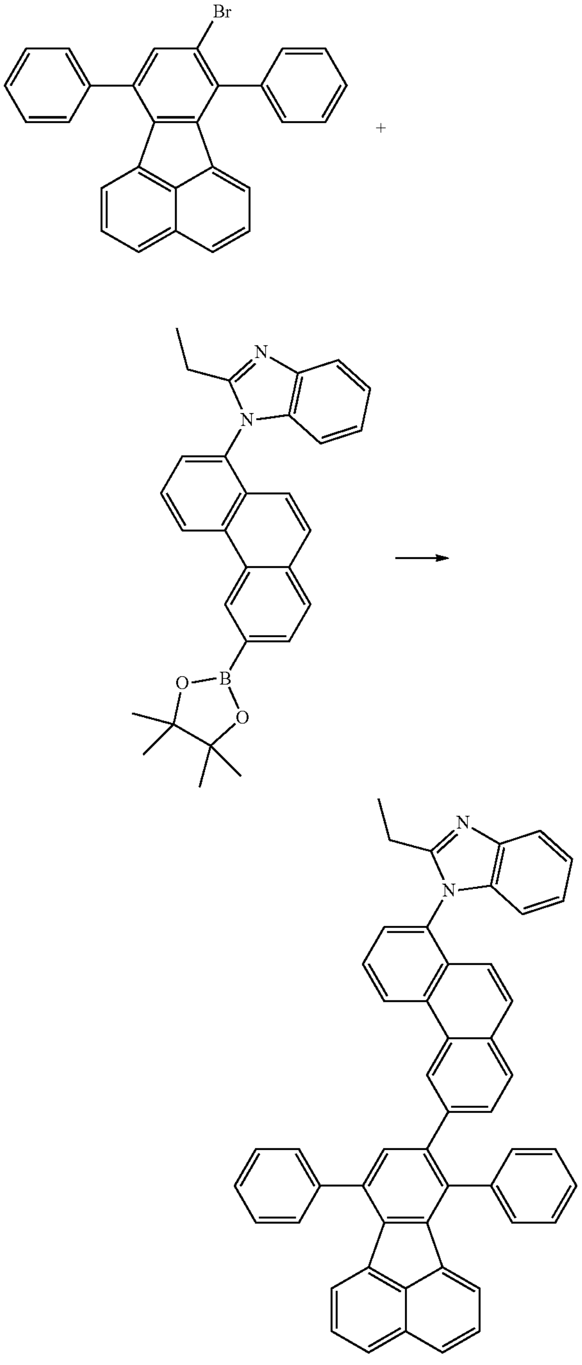

1-7

[Compound 1-7] was prepared in the same manner as in the synthesis method of [Compound 1-1] except that 8-bromo-7,10-diphenylfluoranthene was used instead of 2-(7,10-diphenylfluoranthen-8-yl)-4,4,5,5-tetramethyl-1,3,2-dioxaborolane, and 2-ethyl-1-(6-(4,4,5,5-tetramethyl-1,3,2-dioxaborolan-2-yl)phenanthren-1-yl)-1H-benzo[d]imidazole was used instead of 1-(4-bromophenyl)-2-ethyl-1H-benzo[d]imidazole.

$[M+H]^+=675$

<Synthesis of Compound 1-8>

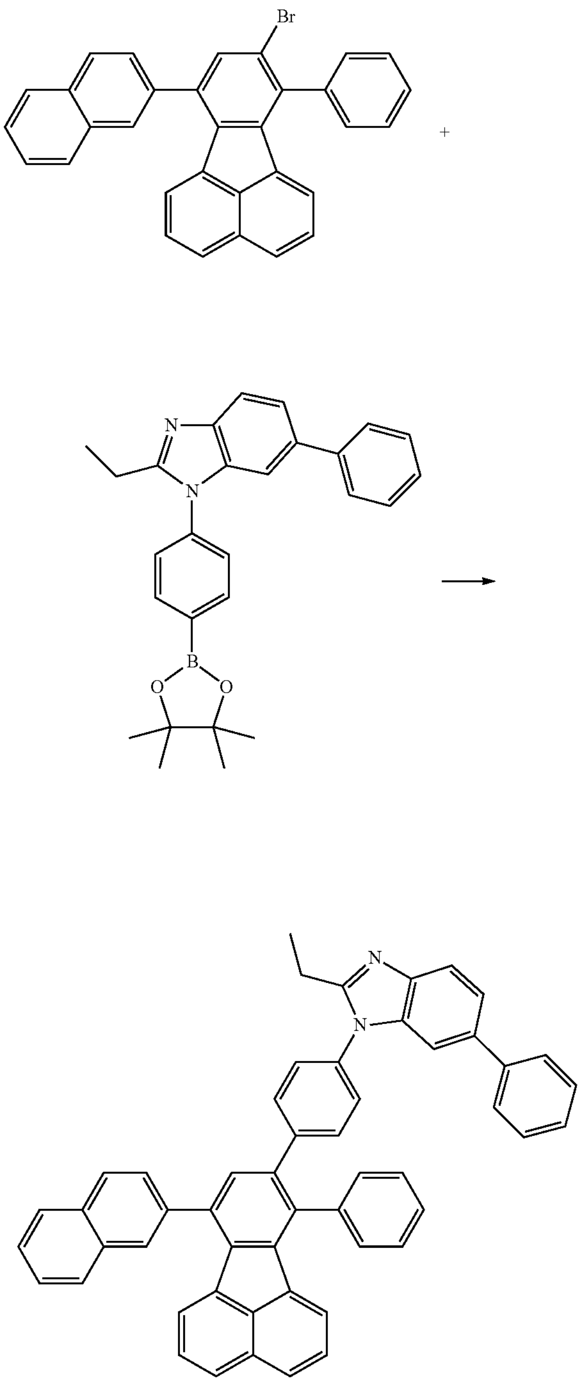

1-8

[Compound 1-8] was prepared in the same manner as in the synthesis method of [Compound 1-1] except that 8-bromo-10-(naphthalen-2-yl)-7-phenylfluoranthene was used instead of 2-(7,10-diphenylfluoranthen-8-yl)-4,4,5,5-tetramethyl-1,3,2-dioxaborolane, and 2-ethyl-6-phenyl-1-(4-(4,4,5,5-tetramethyl-1,3,2-dioxaborolan-2-yl)phenyl)-1H-benzo[d]imidazole was used instead of 1-(4-bromophenyl)-2-ethyl-1H-benzo[d]imidazole.

$[M+H]^+$=701

<Synthesis of Compound 1-9>

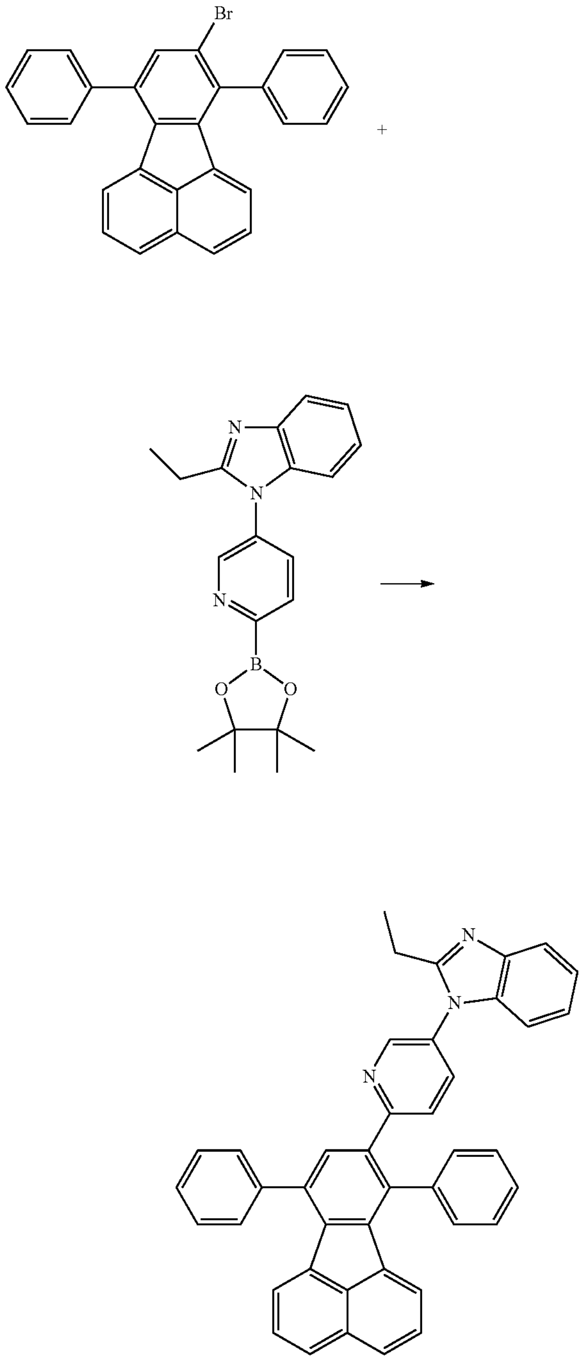

1-9

[Compound 1-9] was prepared in the same manner as in the synthesis method of [Compound 1-1] except that 8-bromo-7,10-diphenylfluoranthene was used instead of 2-(7,10-diphenylfluoranthen-8-yl)-4,4,5,5-tetramethyl-1,3,2-dioxaborolane, and 2-ethyl-1-(6-(4,4,5,5-tetramethyl-1,3,2-dioxaborolan-2-yl)pyridin-3-yl)-1H-benzo[d]imidazole was used instead of 1-(4-bromophenyl)-2-ethyl-1H-benzo[d]imidazole.

$[M+H]^+$=576

<Synthesis of Compound 1-10>

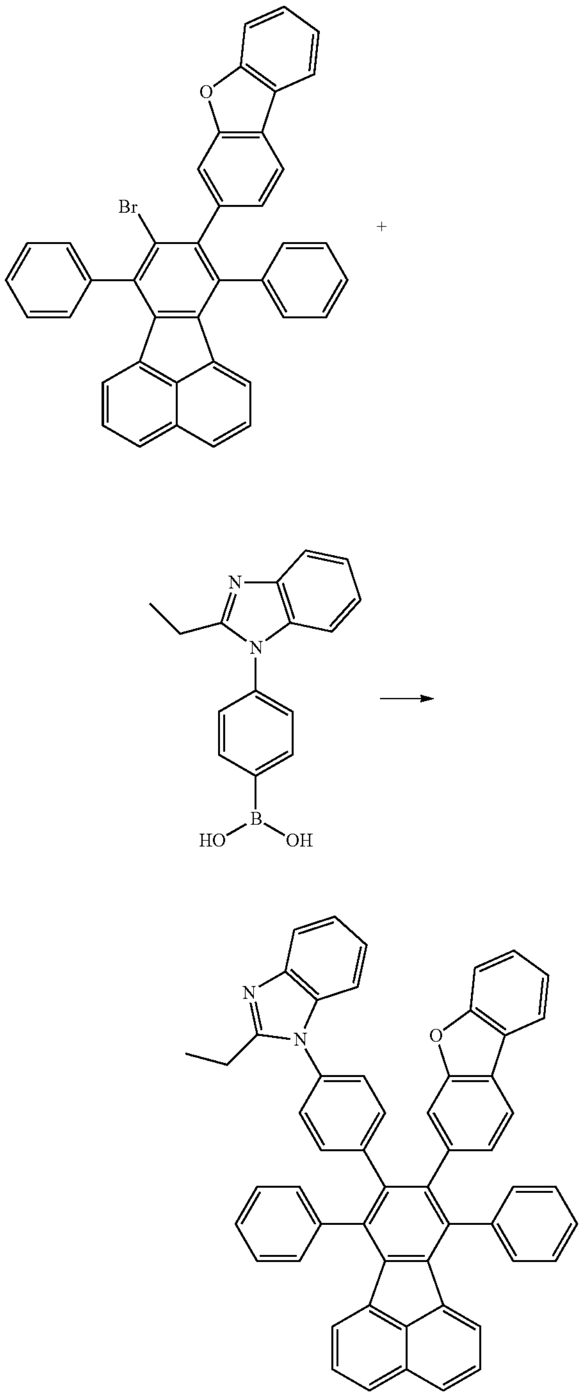

1-10

[Compound 1-10] was prepared in the same manner as in the synthesis method of [Compound 1-1] except that 3-(9-bromo-7,10-diphenylfluoranthen-8-yl)dibenzo[b,d]furan was used instead of 2-(7,10-diphenylfluoranthen-8-yl)-4,4,5,5-tetramethyl-1,3,2-dioxaborolane, and 4-(2-ethyl-1H-benzo[d]imidazol-1-yl)phenyl)boronic acid was used instead of 1-(4-bromophenyl)-2-ethyl-1H-benzo[d]imidazole.

$[M+H]^+$=741

<Synthesis of Compound 1-11>

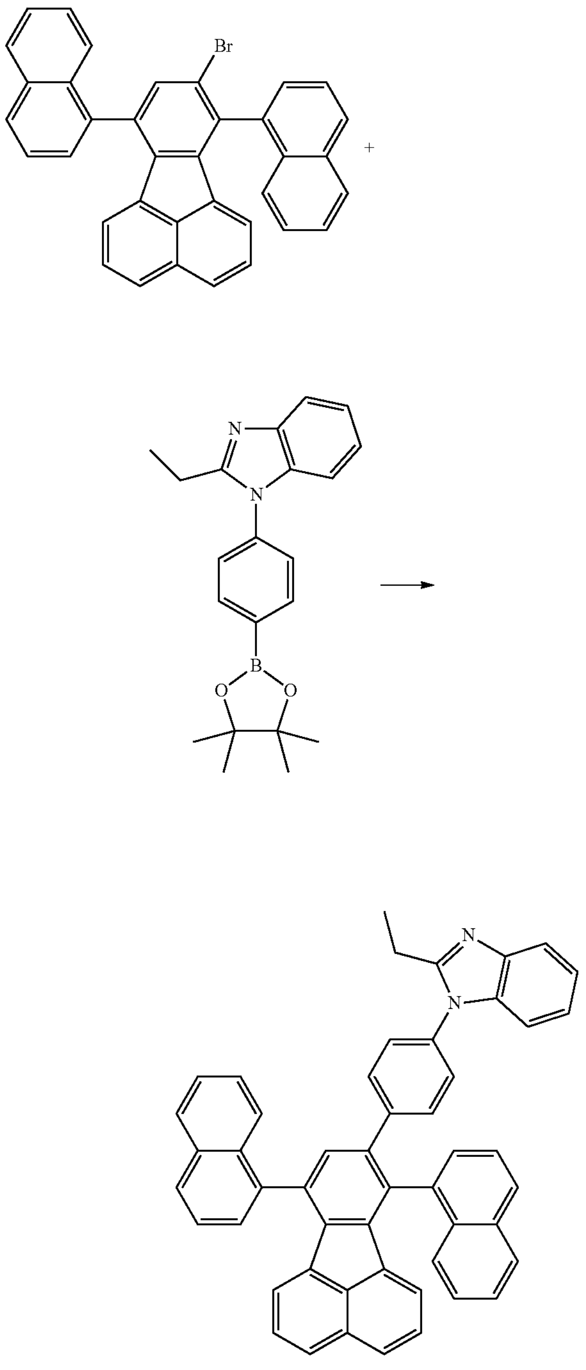

1-11

[Compound 1-11] was prepared in the same manner as in the synthesis method of [Compound 1-1] except that 8-bromo-7,10-di(naphthalen-1-yl)fluoranthene was used instead of 2-(7,10-diphenylfluoranthen-8-yl)-4,4,5,5-tetramethyl-1,3,2-dioxaborolane, and 2-ethyl-1-(4-(4,4,5,5-tetramethyl-1,3,2-dioxaborolan-2-yl)phenyl)-1H-benzo[d]imidazole was used instead of 1-(4-bromophenyl)-2-ethyl-1H-benzo[d]imidazole.

$[M+H]^+$=675

<Synthesis of Compound 1-12>

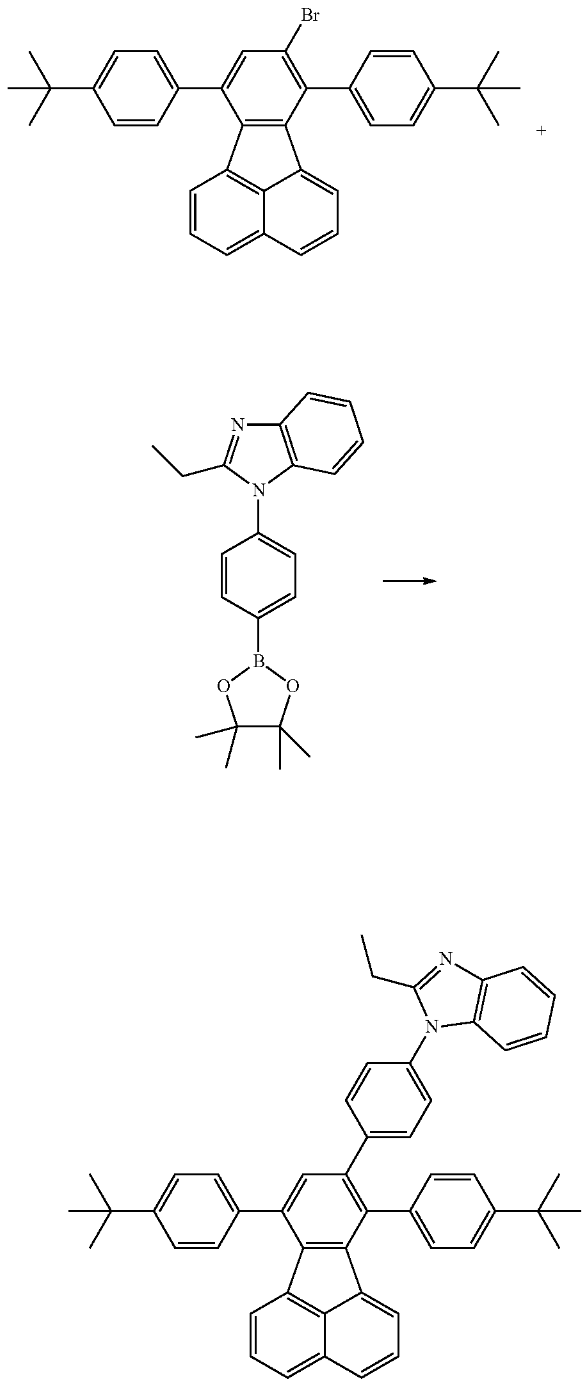

1-12

[Compound 1-12] was prepared in the same manner as in the synthesis method of [Compound 1-1] except that 8-bromo-7,10-bis(4-(tert-butyl)phenyl)fluoranthene was used instead of 2-(7,10-diphenylfluoranthen-8-yl)-4,4,5,5-tetramethyl-1,3,2-dioxaborolane, and 2-ethyl-1-(4-(4,4,5,5-tetramethyl-1,3,2-dioxaborolan-2-yl)phenyl)-1H-benzo[d]imidazole was used instead of 1-(4-bromophenyl)-2-ethyl-1H-benzo[d]imidazole.

$[M+H]^+=687$

<Synthesis of Compound 1-13>

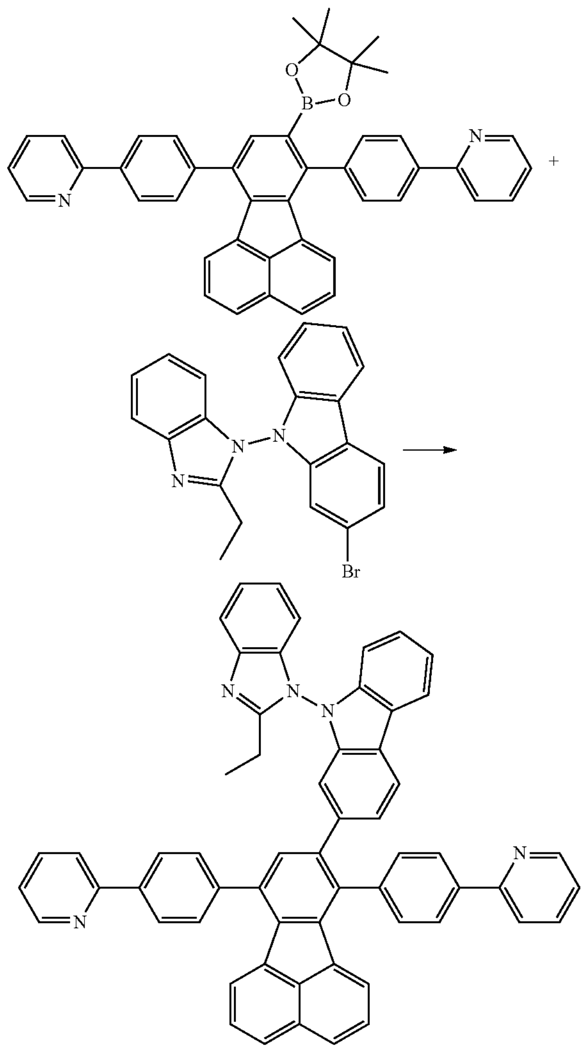

1-13

[Compound 1-13] was prepared in the same manner as in the synthesis method of [Compound 1-1] except that 2,2'-((8-(4,4,5,5-tetramethyl-1,3,2-dioxaborolan-2-yl)fluoranthene-7,10-diyl)bis(4,1-phenylene))dipyridine was used instead of 2-(7,10-diphenylfluoranthen-8-yl)-4,4,5,5-tetramethyl-1,3,2-dioxaborolane, and 2-bromo-9-(2-ethyl-1H-benzo[d]imidazol-1-yl)-9H-carbazole was used instead of 1-(4-bromophenyl)-2-ethyl-1H-benzo[d]imidazole.

$[M+H]^+=818$

<Synthesis of Compound 1-14>

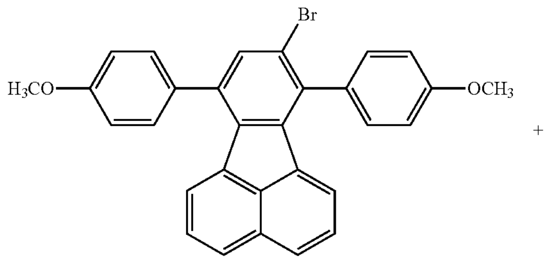

-continued

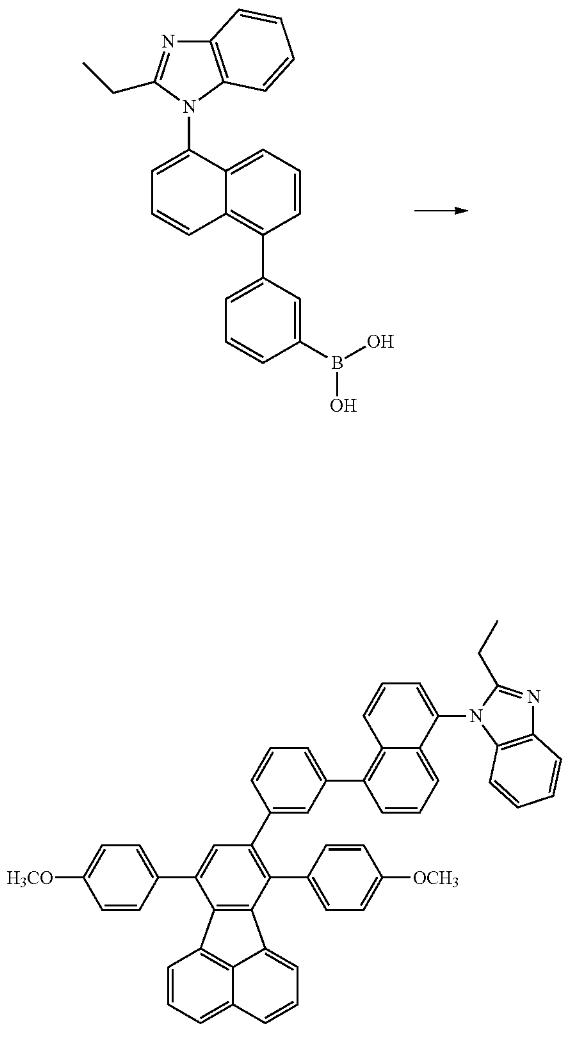

1-14

[Compound 1-14] was prepared in the same manner as in the synthesis method of [Compound 1-1] except that 8-bromo-7,10-bis(4-methoxyphenyl)fluoranthene was used instead of 2-(7,10-diphenylfluoranthen-8-yl)-4,4,5,5-tetramethyl-1,3,2-dioxaborolane, and (3-(5-(2-ethyl-1H-benzo[d]imidazol-1-yl)naphthalen-1-yl)phenyl)boronic acid was used instead of 1-(4-bromophenyl)-2-ethyl-1H-benzo[d]imidazole.

$[M+H]^+=761$

<Synthesis of Compound 1-15>

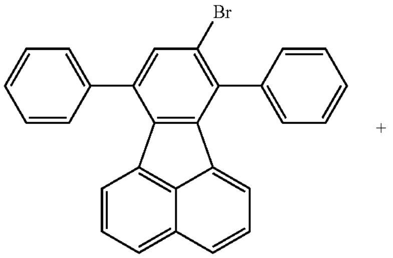

-continued

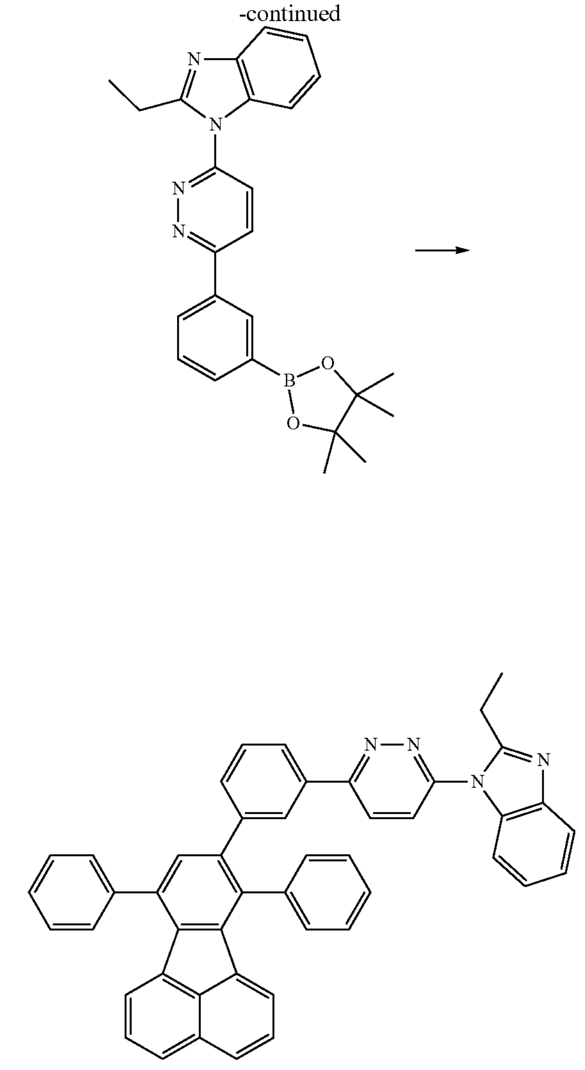

1-15

[Compound 1-15] was prepared in the same manner as in the synthesis method of [Compound 1-1] except that 8-bromo-7,10-diphenylfluoranthene was used instead of 2-(7,10-diphenylfluoranthen-8-yl)-4,4,5,5-tetramethyl-1,3,2-dioxaborolane, and 2-ethyl-1-(6-(3-(4,4,5,5-tetramethyl-1,3,2-dioxaborolan-2-yl)phenyl)pyridazin-3-yl)-1H-benzo[d]imidazole was used instead of 1-(4-bromophenyl)-2-ethyl-1H-benzo[d]imidazole.

$[M+H]^+=653$

<Synthesis of Compound 1-16>

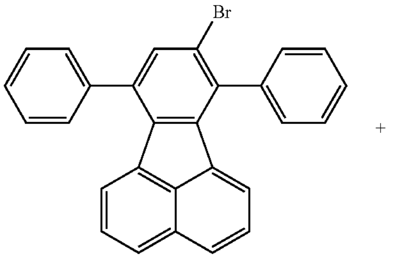

-continued

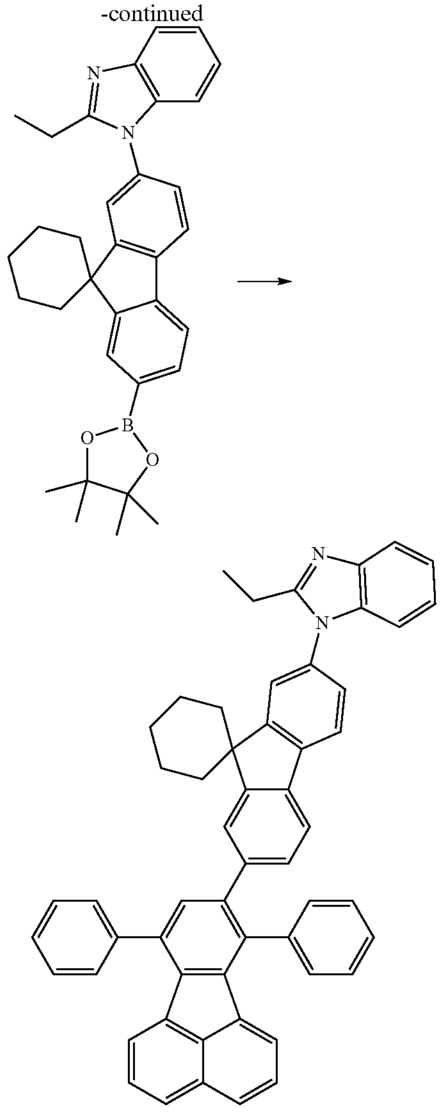

1-16

[Compound 1-16] was prepared in the same manner as in the synthesis method of [Compound 1-1] except that 8-bromo-7,10-diphenylfluoranthene was used instead of 2-(7,10-diphenylfluoranthen-8-yl)-4,4,5,5-tetramethyl-1,3,2-dioxaborolane, and 2-ethyl-1-(2'-(4,4,5,5-tetramethyl-1,3,2-dioxaborolan-2-yl)spiro[cyclohexane-1,9'-fluoren]-7'-yl)-1H-benzo[d]imidazole was used instead of 1-(4-bromophenyl)-2-ethyl-1H-benzo[d]imidazole.

$[M+H]^+=731$

<Synthesis of Compound 1-17>

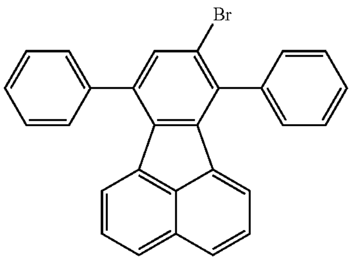

+

-continued

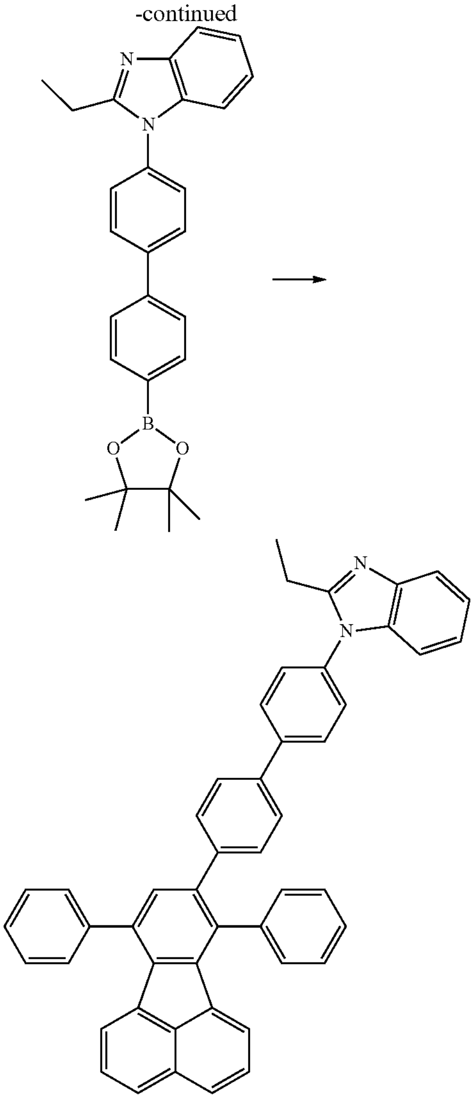

1-17

[Compound 1-17] was prepared in the same manner as in the synthesis method of [Compound 1-1] except that 8-bromo-7,10-diphenylfluoranthene was used instead of 2-(7,10-diphenylfluoranthen-8-yl)-4,4,5,5-tetramethyl-1,3,2-dioxaborolane, and 2-ethyl-1-(4'-(4,4,5,5-tetramethyl-1,3,2-dioxaborolan-2-yl)-[1,1'-biphenyl]-4-yl)-1H-benzo[d]imidazole was used instead of 1-(4-bromophenyl)-2-ethyl-1H-benzo[d]imidazole.

$[M+H]^+=651$

Example 1

A glass substrate on which indium tin oxide (ITO) was coated as a thin film to a thickness of 100 nm was placed in distilled water containing dissolved detergent and ultrasonically cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. The substrate was cleaned for 5 minutes using oxygen plasma, and then transferred to a vacuum deposition apparatus.

On the transparent ITO electrode prepared as above, the following Compound HI-A was thermal vacuum deposited to a thickness of 60 nm to form a hole injection layer.

On the hole injection layer, the following Compound HAT was vacuum deposited to form a first hole transfer layer having a thickness of 5 nm, and the following Compound HT-A was vacuum deposited on the first hole transfer layer to form a second hole transfer layer having a thickness of 50 nm.

Subsequently, the following compounds Compound BH and Compound BD were vacuum deposited on the second hole transfer layer in a weight ratio of 25:1 to form a light emitting layer having a thickness of 20 nm.

On the light emitting layer, [Compound 1-1] and the following Compound LiQ were vacuum deposited in a weight ratio of 1:1 to form an electron injection and transfer layer having a thickness of 35 nm.

A cathode was formed on the electron injection and transfer layer by depositing lithium fluoride (LiF) to a thickness of 1 nm and then depositing aluminum to a thickness of 100 nm, and as a result, an organic light emitting device was manufactured.

In the above-described process, the deposition rates of the organic materials were maintained at 0.04 nm/sec to 0.09 nm/sec, the deposition rate of the lithium fluoride was maintained at 0.03 nm/sec, and the deposition rate of the aluminum was maintained at 0.2 nm/sec. The degree of vacuum during the deposition was maintained at $1\times10^{-7}$ torr to $5\times10^{-5}$ torr.

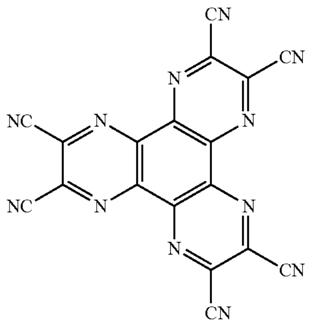

HAT

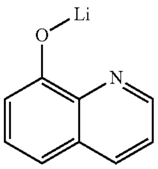

LiQ

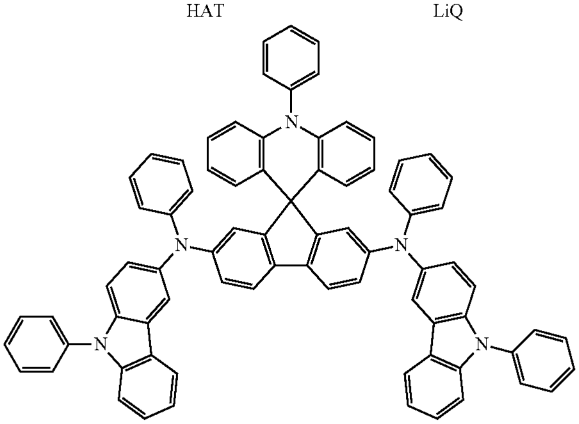

HI-A

-continued

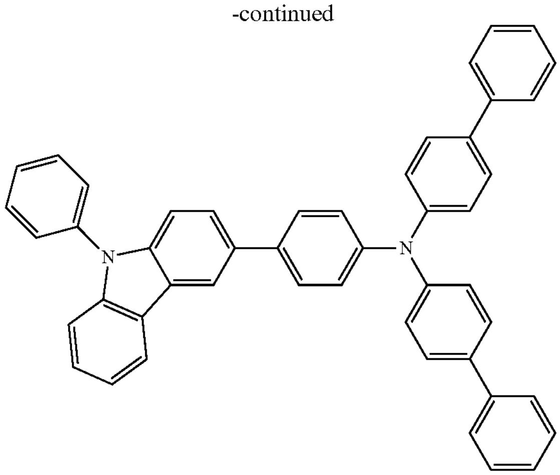

HT-A

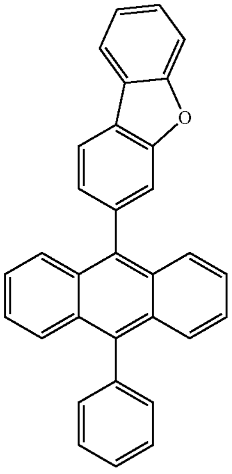

BH

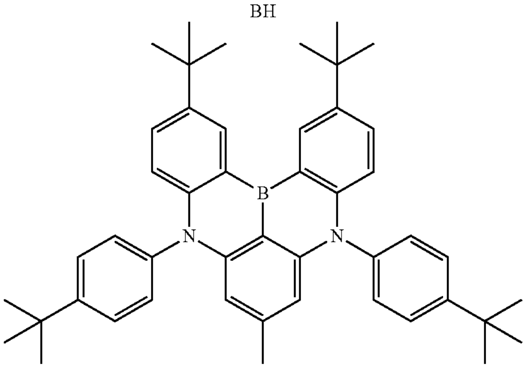

BD

Examples 2 to 17

Organic light emitting devices were manufactured in the same manner as in Example 1 except that compounds of the following Table 1 were used instead of [Compound 1-1] of Example 1.

Comparative Examples 1 to 8

Organic light emitting devices were manufactured in the same manner as in Example 1 except that compounds of the following Table 1 were used instead of [Compound 1-1] of Example 1.

E1
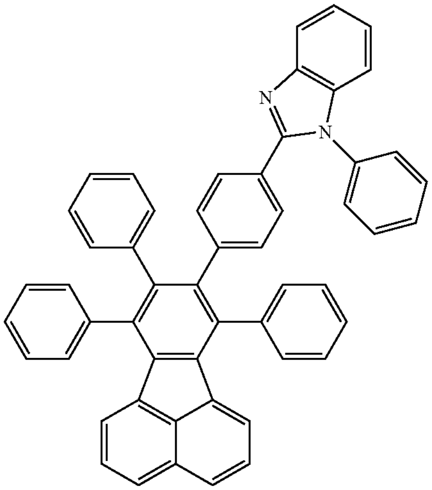
E2
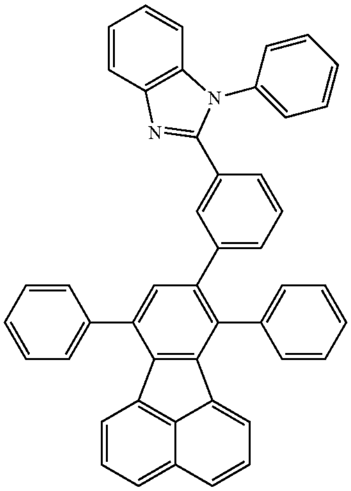
E3
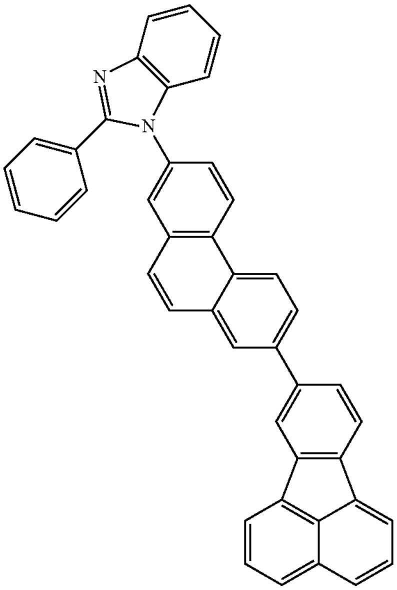
-continued
E4
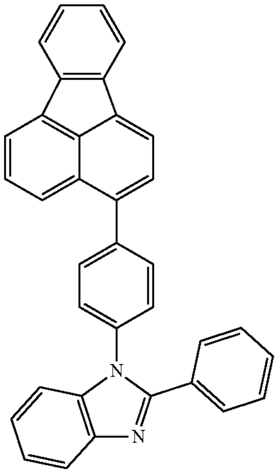
E5
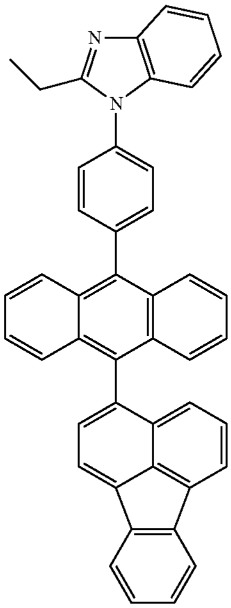

-continued

E6

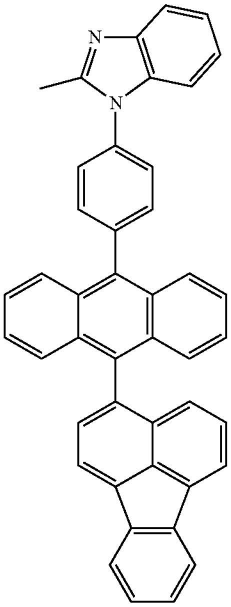

E7

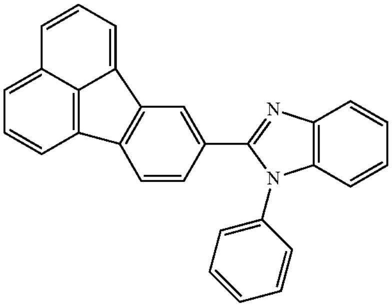

E8

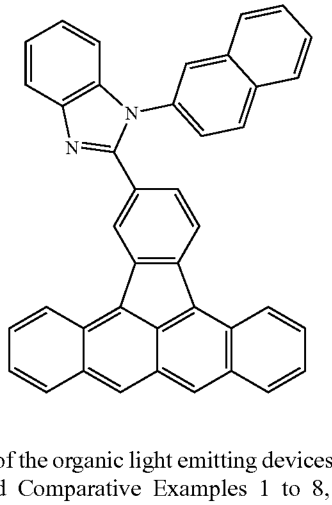

For each of the organic light emitting devices of Examples 1 to 17 and Comparative Examples 1 to 8, voltage and efficiency were measured under current density of 10 $mA/cm^2$, lifetime ($LT_{95}$) was measured under current density of 20 $mA/cm^2$, and the results are shown in the following Table 1. Herein, $LT_{95}$ means time taken for luminance to become 95% with respect to initial luminance. Color coordinate (x, y) means a CIE color coordinate.

TABLE 1

| | Electron Injection and Transfer Layer | Driving Voltage (V) | Efficiency (cd/A) | Color Coordinate (x, y) | $LT_{95}$ (h) |
|---|---|---|---|---|---|
| Example 1 | Compound 1-1 | 3.93 | 5.09 | (0.142, 0.097) | 280 |
| Example 2 | Compound 1-2 | 3.98 | 5.11 | (0.142, 0.097) | 273 |
| Example 3 | Compound 1-3 | 4.03 | 5.14 | (0.142, 0.096) | 289 |
| Example 4 | Compound 1-4 | 4.07 | 5.00 | (0.142, 0.097) | 274 |
| Example 5 | Compound 1-5 | 4.04 | 5.14 | (0.142, 0.097) | 295 |
| Example 6 | Compound 1-6 | 4.02 | 5.02 | (0.142, 0.096) | 284 |
| Example 7 | Compound 1-7 | 3.99 | 5.07 | (0.142, 0.097) | 290 |
| Example 8 | Compound 1-8 | 4.02 | 5.02 | (0.142, 0.096) | 287 |
| Example 9 | Compound 1-9 | 4.01 | 5.01 | (0.142, 0.096) | 298 |
| Example 10 | Compound 1-10 | 4.02 | 5.08 | (0.142, 0.096) | 294 |
| Example 11 | Compound 1-11 | 4.04 | 5.00 | (0.142, 0.096) | 288 |
| Example 12 | Compound 1-12 | 4.00 | 4.95 | (0.142, 0.097) | 300 |
| Example 13 | Compound 1-13 | 4.10 | 5.02 | (0.142, 0.097) | 292 |
| Example 14 | Compound 1-14 | 4.06 | 5.04 | (0.142, 0.097) | 287 |
| Example 15 | Compound 1-15 | 4.07 | 5.04 | (0.142, 0.097) | 305 |
| Example 16 | Compound 1-16 | 4.02 | 5.08 | (0.142, 0.097) | 287 |
| Example 17 | Compound 1-17 | 4.02 | 5.06 | (0.142, 0.097) | 305 |
| Comparative Example 1 | Compound E1 | 4.32 | 4.50 | (0.142, 0.097) | 150 |
| Comparative Example 2 | Compound E2 | 4.28 | 4.68 | (0.142, 0.097) | 158 |
| Comparative Example 3 | Compound E3 | 4.38 | 4.24 | (0.142, 0.096) | 150 |
| Comparative Example 4 | Compound E4 | 4.22 | 4.62 | (0.142, 0.097) | 144 |
| Comparative Example 5 | Compound E5 | 4.27 | 4.48 | (0.142, 0.097) | 147 |
| Comparative Example 6 | Compound E6 | 4.30 | 4.46 | (0.142, 0.096) | 149 |
| Comparative Example 7 | Compound E7 | 4.24 | 4.59 | (0.142, 0.097) | 136 |
| Comparative Example 8 | Compound E8 | 4.40 | 4.42 | (0.142, 0.097) | 169 |

As described in Table 1, the compound of Chemical Formula 1 according to the present disclosure can be included in an electron injection and transfer layer of an organic light emitting device. When comparing the compounds of Examples 1 to 17 and the compounds of Comparative Examples 1, 2, 7 and 8 of Table 1, it was identified that the compound in which the bonding position where benzimidazole bonds to fluoranthene is N was significantly superior in terms of voltage, efficiency and lifetime of the organic light emitting device compared to the compound in which carbon between N and N of the benzimidazole bonds.

In addition, when comparing the examples and Comparative Example 3 of Table 1, it was identified that the compound of Chemical Formula 1 according to the present disclosure was significantly superior in terms of voltage, efficiency and lifetime of the organic light emitting device compared to the compound in which Ar1 and Ar2 are hydrogen.

When comparing the examples and Comparative Examples 4 to 6 of Table 1, it was identified that the compound in which the bonding position where fluoranthene bonds to benzimidazole is No. 8 carbon was significantly superior in terms of voltage, efficiency and lifetime of the organic light emitting device compared to the compound in which No. 3 carbon of the fluoranthene bonds.

The invention claimed is:

1. A compound of Chemical Formula 1:

[Chemical Formula 1]

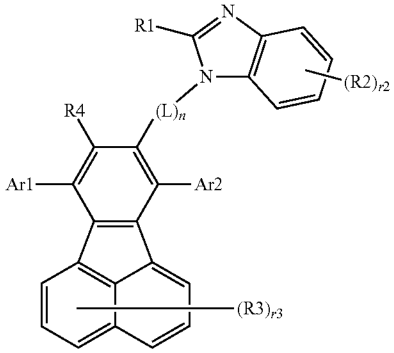

wherein, in Chemical Formula 1:

L is a direct bond, a substituted or unsubstituted arylene group, or a substituted or unsubstituted heteroarylene group;

n is 1 or 2, and when n is 2, the Ls are the same as or different from each other;

R1 to R4 are the same as or different from each other, and are each independently hydrogen, deuterium, a substituted or unsubstituted alkyl group, a substituted or unsubstituted aryl group; or a substituted or unsubstituted heteroaryl group;

r2 is 4, and the R2s are the same as or different from each other;

r3 is 6, and 3s are the same as or different from each other; and

Ar1 and Ar2 are the same as or different from each other, and each independently is a substituted or unsubstituted aryl group.

2. The compound of claim 1, wherein L is a direct bond, a phenylene group, a naphthylene group, a biphenylylene group, a divalent phenanthrene group, a divalent phenalene group, a divalent pyrene group, a divalent fluoranthene group, a divalent dimethylfluorenyl group, a divalent spirocyclohexanefluorene group, a divalent pyridine group, a divalent pyridazine group, a divalent carbazole group, a divalent dibenzothiophene group, a divalent t-benzothiophene group, or a divalent quinazoline group.

3. The compound of claim 1, wherein R1 is an alkyl group having 2 to 10 carbon atoms.

4. The compound of claim 1, wherein Ar1 and Ar2 are the same as or different from each other, and are each independently an aryl group that is unsubstituted or substituted with one or more substituents selected from the group consisting of an alkyl group, an alkoxy group, an aryl group, and a heteroaryl group.

5. The compound of claim 1, wherein the compound of Chemical Formula 1 is any one compound selected from among the following compounds:

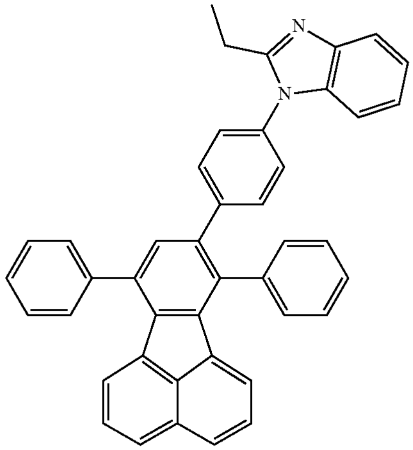

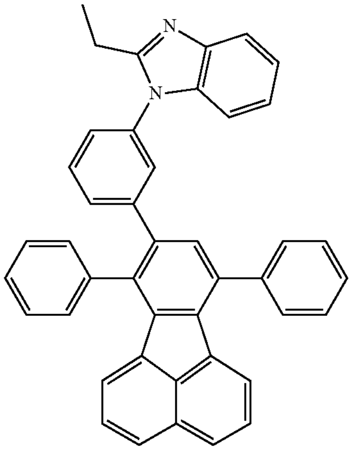

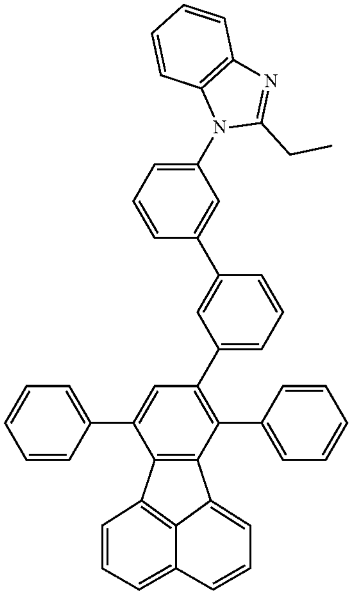

-continued
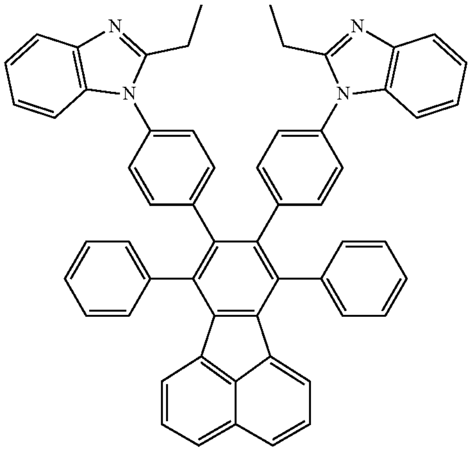
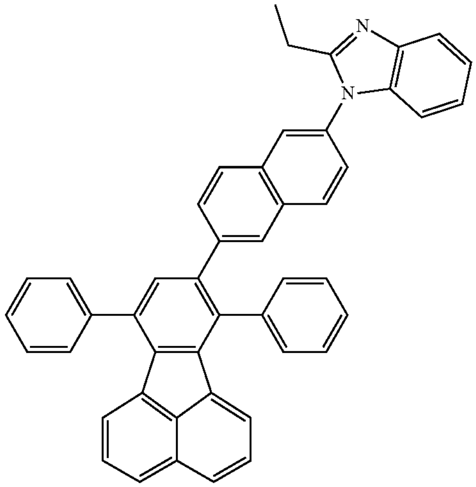
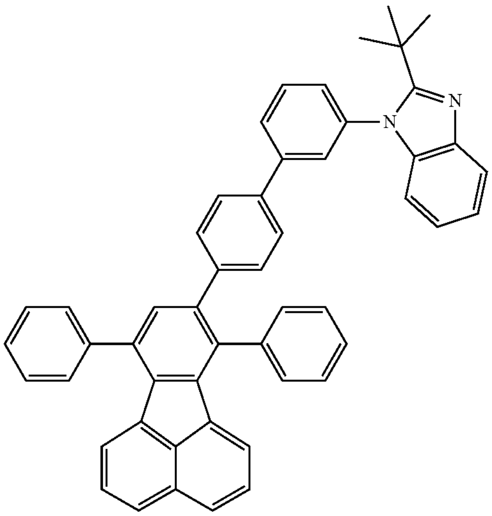
-continued
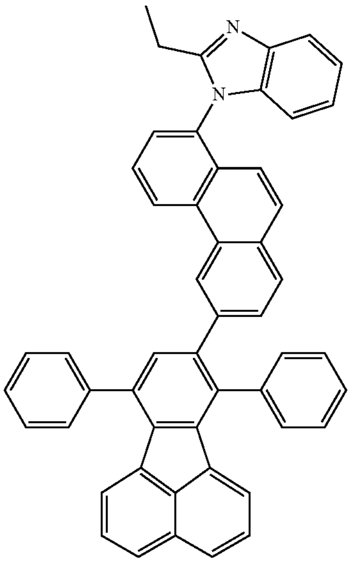
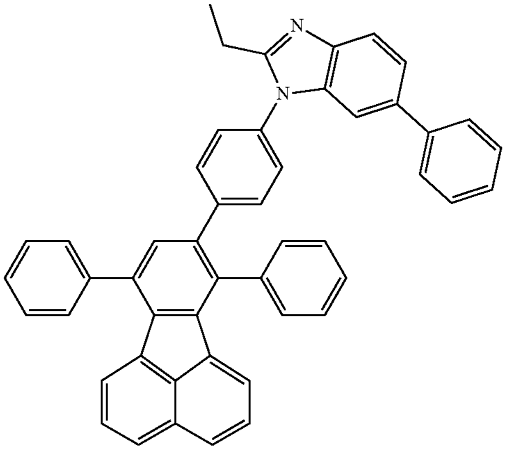
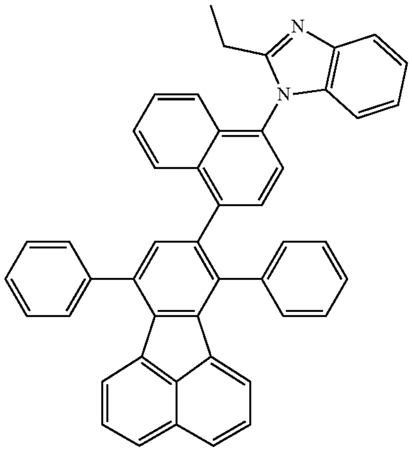

-continued
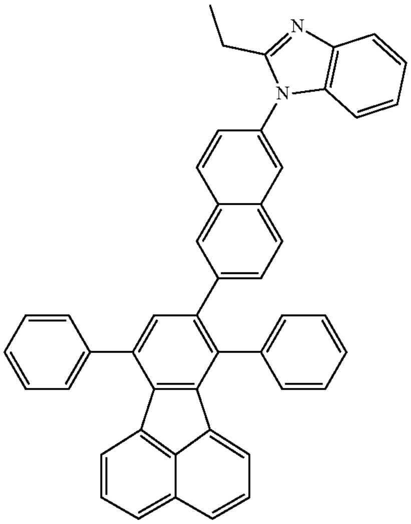
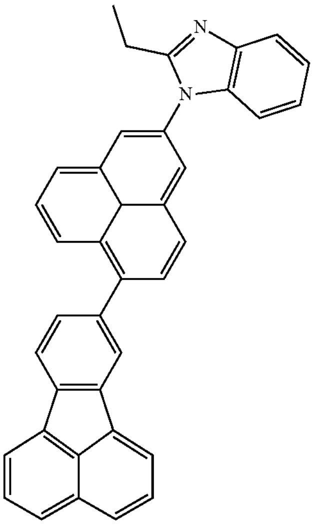
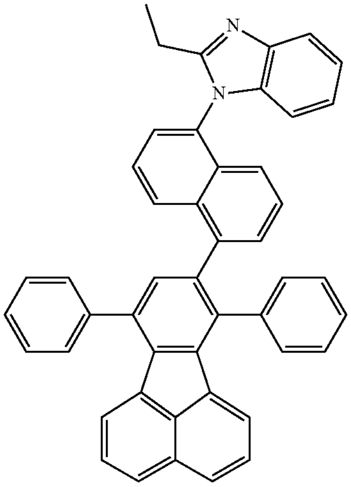
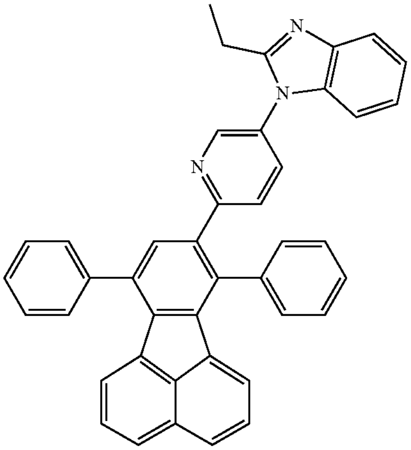
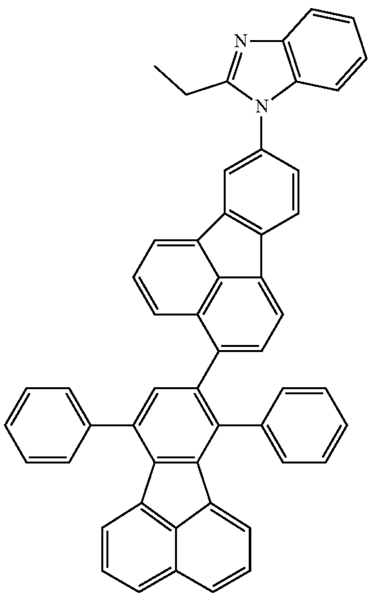
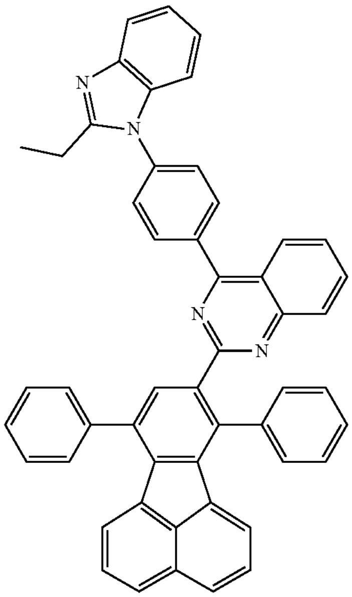

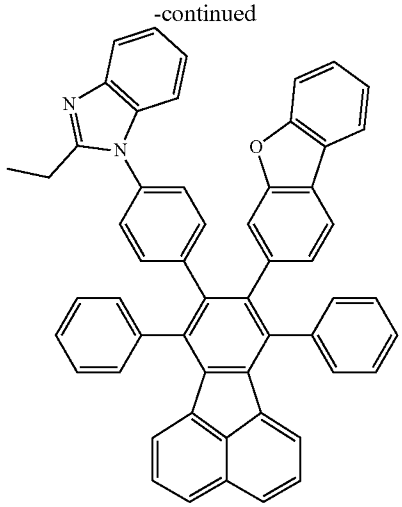
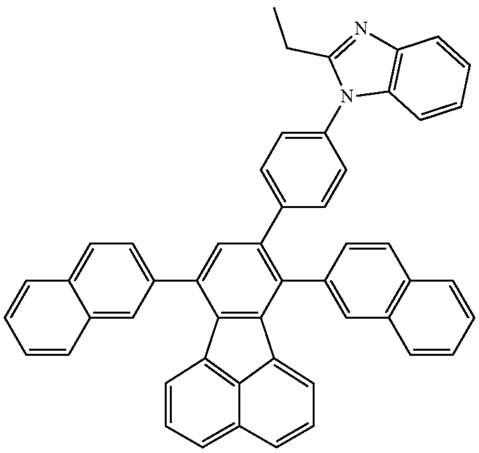
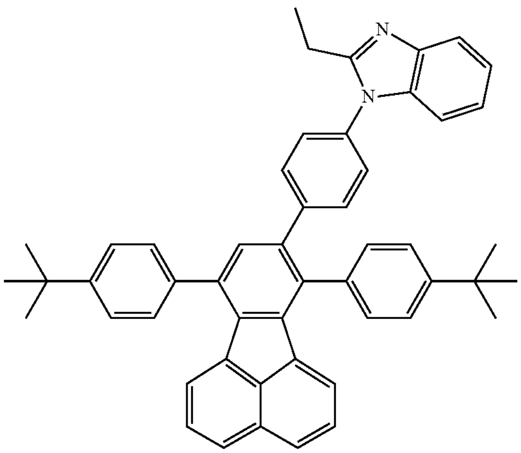
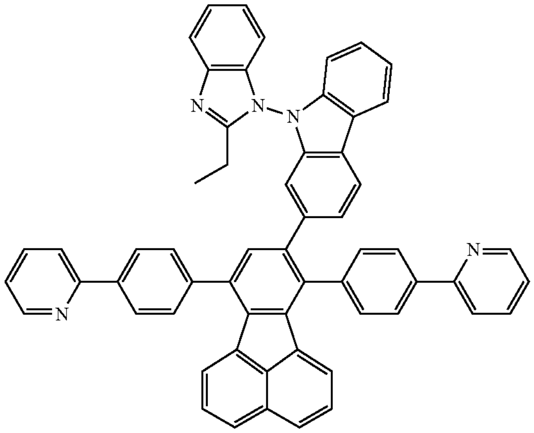
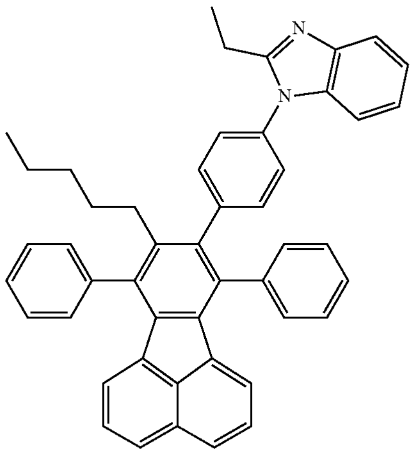
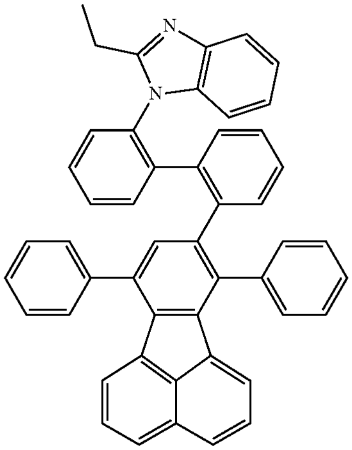

-continued
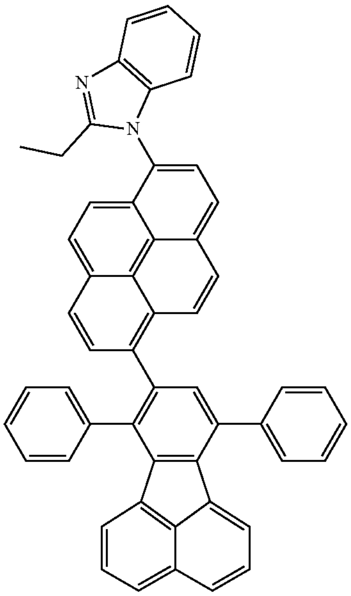
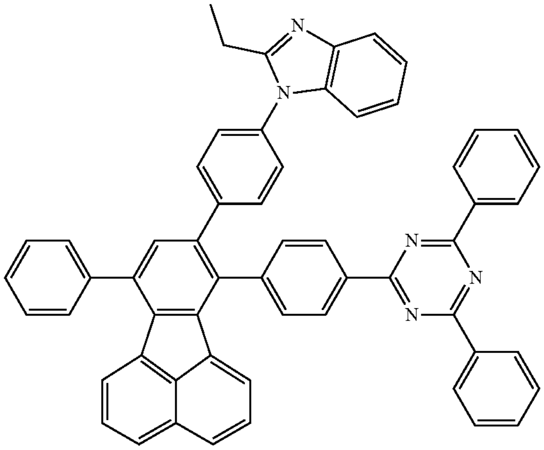
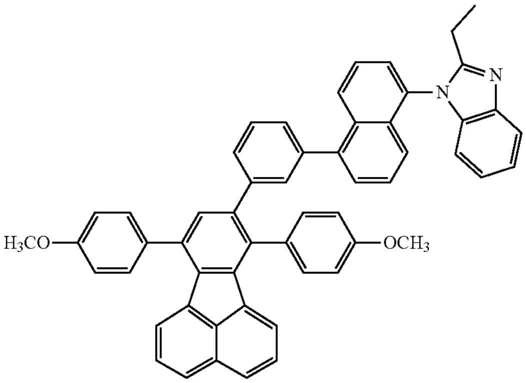
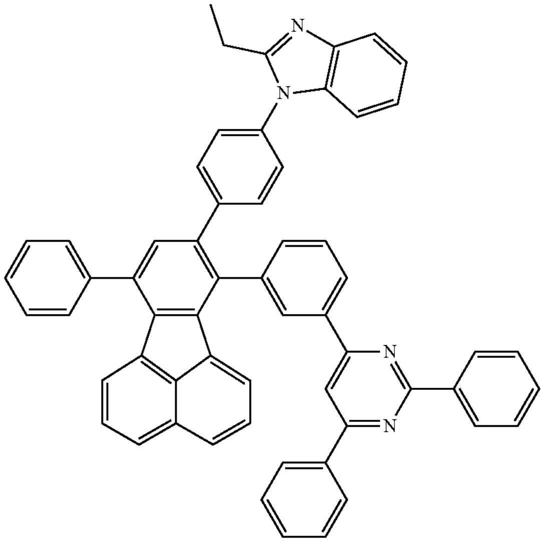
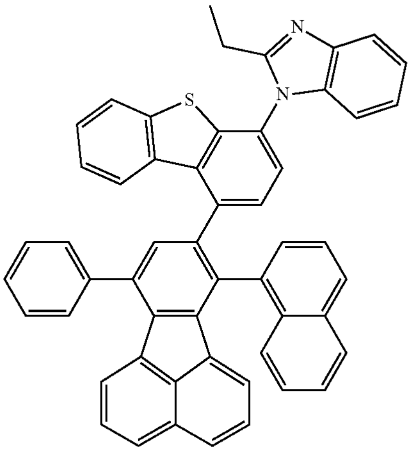
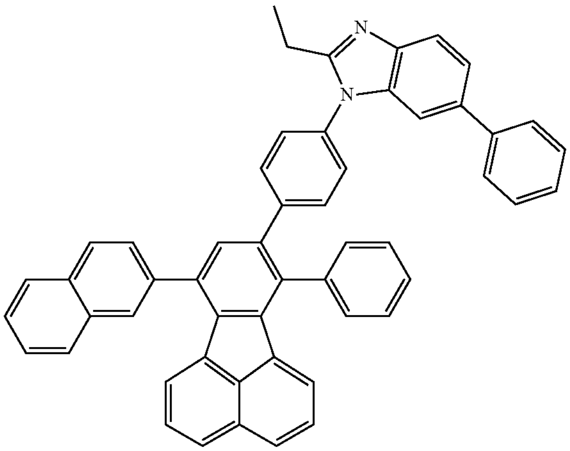

-continued
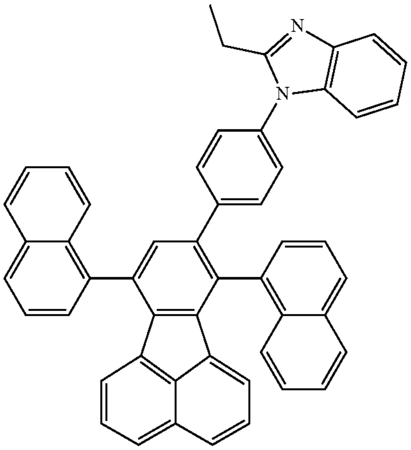
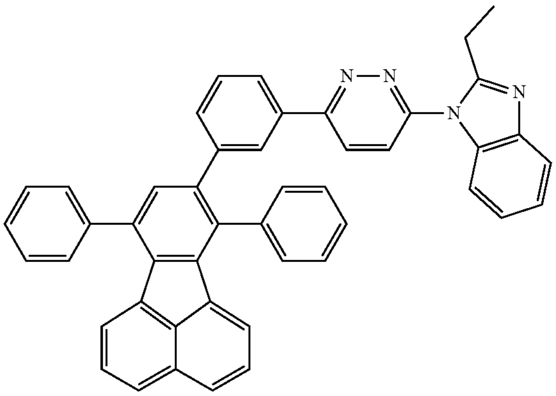
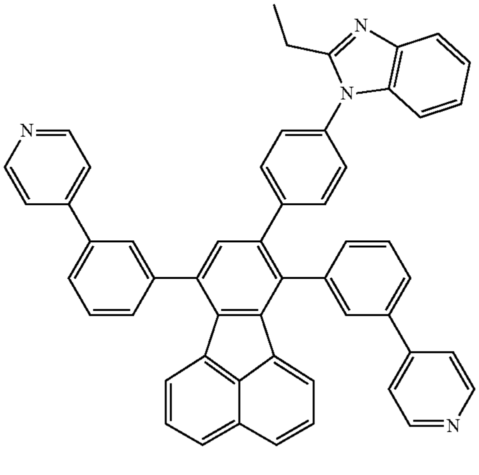
-continued
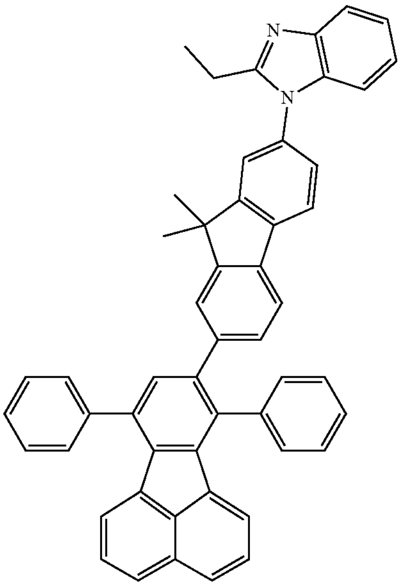
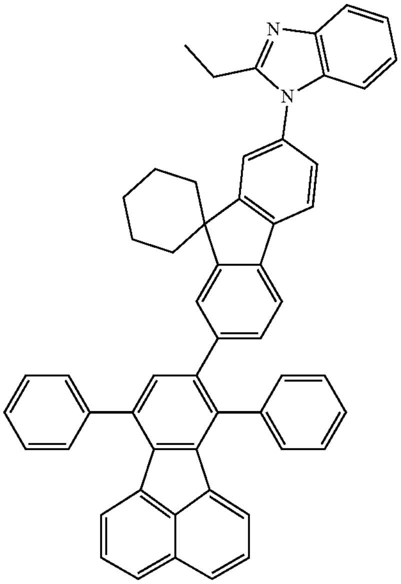
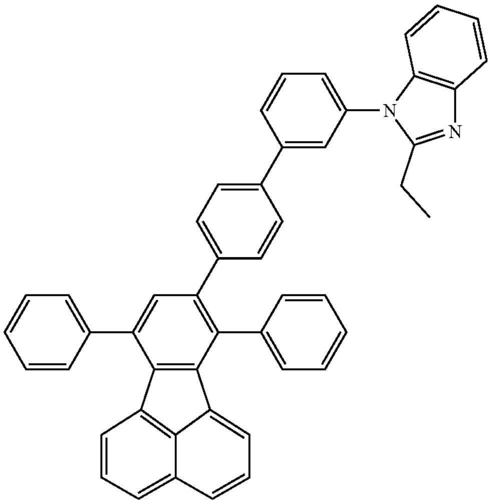 [SMILES: CCc1nc2ccccc2n1-c1cccc(-c2ccc(-c3cc(-c4ccccc4)c4c(c3-c3ccccc3)-c3cccc5cccc-4c35)cc2)c1]

-continued

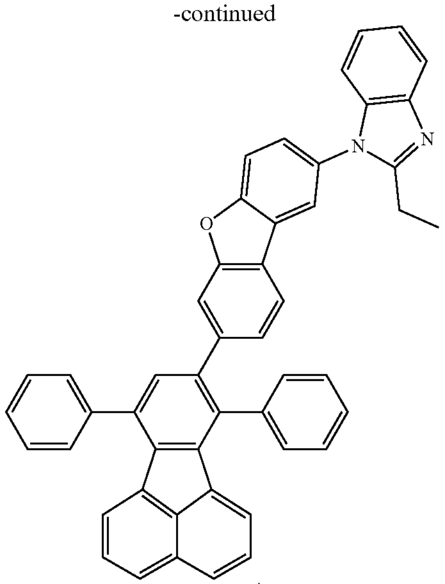

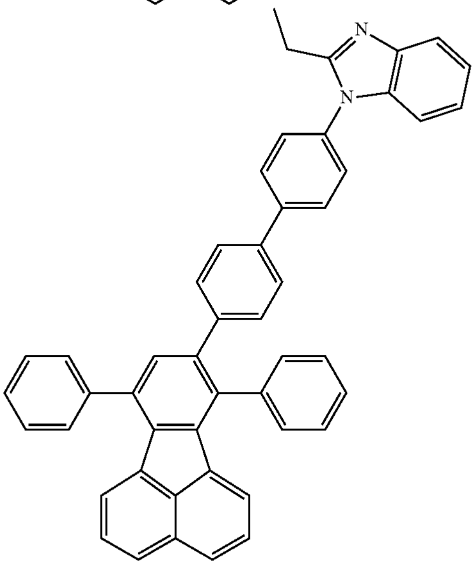

-continued

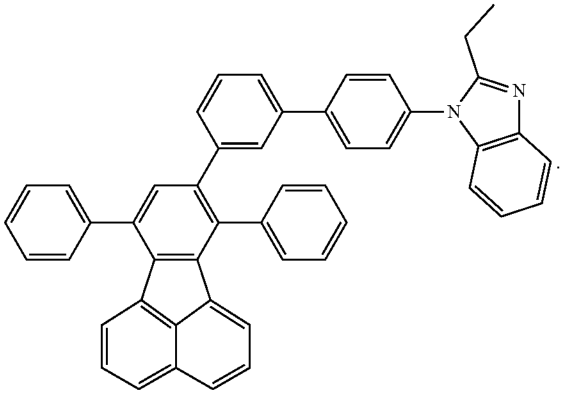

6. An organic light emitting device comprising:

a first electrode;

a second electrode provided opposite to the first electrode; and one or more organic material layers provided between the first electrode and the second electrode, wherein at least one of the organic material layers includes the compound of claim 1.

7. The organic light emitting device of claim 6, wherein:

the organic material layer includes a hole blocking layer, an electron injection layer, an electron transfer layer, or an electron injection and transfer layer; and the hole blocking layer, the electron injection layer, the electron transfer layer, or the electron injection and transfer layer includes the compound.

* * * * *